(12) United States Patent
Chancellor et al.

(10) Patent No.: US 7,115,417 B1
(45) Date of Patent: *Oct. 3, 2006

(54) SOFT TISSUE AND BONE AUGMENTATION AND BULKING UTILIZING MUSCLE-DERIVED PROGENITO COMPOSITIONS, AND TREATMENTS THEREOF

(76) Inventors: Michael B. Chancellor, 5836 Ferree St., Pittsburg, PA (US) 15217; Johnny Huard, 6412 Howe St., Pittsburgh, PA (US) 15206; Christopher C. Capelli, 4500 7th St., Kenosha, WI (US) 53142; Zhuqing Qu, 5551 Center Ave., Apt. 708, Pittsburgh, PA (US) 15232

( * ) Notice: Subject to any disclaimer, the term of this patent is extended or adjusted under 35 U.S.C. 154(b) by 0 days.

This patent is subject to a terminal disclaimer.

(21) Appl. No.: 09/549,937

(22) Filed: Apr. 14, 2000

Related U.S. Application Data

(63) Continuation-in-part of application No. 09/302,896, filed on Apr. 30, 1999, now Pat. No. 6,866,842.

(60) Provisional application No. 60/083,917, filed on May 1, 1998.

(51) Int. Cl.
- C12N 5/00 (2006.01)
- C12N 5/02 (2006.01)
- C12N 5/06 (2006.01)
- C12N 5/08 (2006.01)

(52) U.S. Cl. .................. 435/383; 435/325; 435/354; 435/366

(58) Field of Classification Search ............ 435/325, 435/378, 366, 352, 353, 354, 355, 372, 395, 435/402, 383; 424/93.1, 93.2, 93.21
See application file for complete search history.

(56) References Cited

U.S. PATENT DOCUMENTS

| | | | |
|---|---|---|---|
| 4,424,208 A | 1/1984 | Wallace et al. ............. 424/177 |
| 4,965,353 A | 10/1990 | Della Valle et al. ....... 536/55.1 |
| 5,053,050 A | 10/1991 | Itay ............................. 623/16 |
| 5,130,141 A | 7/1992 | Law et al. ................... 424/548 |
| 5,206,028 A * | 4/1993 | Li .............................. 424/484 |
| 5,336,263 A | 8/1994 | Ersek et al. ................. 623/11 |
| 5,516,532 A | 5/1996 | Atala et al. ................ 424/548 |
| 5,538,722 A | 7/1996 | Blau et al. .............. 424/93.21 |
| 5,594,032 A | 1/1997 | Gonzalez-Cadavid et al. ......................... 514/645 |
| 5,667,778 A * | 9/1997 | Atala ........................ 424/93.7 |
| 5,833,978 A | 11/1998 | Tremblay .................. 424/93.7 |
| 5,858,351 A | 1/1999 | Podsakoff et al. ......... 424/93.2 |
| 5,858,390 A | 1/1999 | Boss, Jr. .................... 424/426 |
| 5,876,447 A | 3/1999 | Arnett ......................... 623/11 |
| 6,001,654 A * | 12/1999 | Anderson et al. ........... 435/377 |
| 6,261,832 B1 * | 7/2001 | Law ......................... 435/286.5 |
| 6,866,842 B1 * | 3/2005 | Chancellor et al. ........ 424/93.1 |

| | | | |
|---|---|---|---|
| 2002/0155096 A1 | 10/2002 | Chancellor et al. |

FOREIGN PATENT DOCUMENTS

| | | |
|---|---|---|
| WO | WO 96/18303 | 6/1986 |
| WO | WO 91/07992 | 6/1991 |
| WO | WO 94/07999 | 4/1994 |
| WO | WO 94/21299 | 9/1994 |
| WO | WO 98/54301 | 3/1998 |
| WO | WO 98/36055 | 8/1998 |
| WO | WO 98/44142 | 8/1998 |
| WO | WO 99/56785 * | 4/1999 |
| WO | WO 99/47163 | 9/1999 |
| WO | WO 99/56785 | 11/1999 |

OTHER PUBLICATIONS

Stem Cells, website;http://www.nih.nih.gov/news/stemcell, 2002, ES1-10,23-42 and Appendex D1.*
JH Martini et al., Anatomy and Physiology, 3$^{rd}$ Ed., Simon & Schuster Company, 1995, p. 315.*
J Kuby, Immunology, 2$^{nd}$ Ed. WH Freeman Company, 1994, pp. 559-560.*
T Y okoyama et al., Tissue Engineering, "Autologous Primary Muscle-Derived Cells Transfer into the Lower Urinary Tract," 2001, vol. 7, No. 4, pp. 395-404.*
T Yokoyama et al., Urology, "Muscle-Derived Cell Transplantation and Differentiation into Lower Urinary Tract Smooth Muscle," 2001, 57:826-831.*
JY Lee et al., Journal of Cell Biology, "Clonal Isolation of Muscle-derived Cells Capable of Enhancing Muscle Regeneration and Bone Healing," Sep. 2000, vol. 150, No. 5, pp. 1085-1099.*
Jacques P. Tremblay et al., Basic Appl. Myol. 7 (3&4): pp. 221-230, 1997.*
Fred D. Ledley, Pharmaceutical Research, vol. 13, No. 11, 1996, pp. 1595-1614.*

(Continued)

*Primary Examiner*—Brian Whiteman
(74) *Attorney, Agent, or Firm*—Mintz, Levin, Cohn, Ferris, Glovsky, and Popeo PC; Leslie Serunian; Ivor Elrifi

(57) ABSTRACT

The present invention provides muscle-derived progenitor cells that show long-term survival following transplantation into body tissues and which can augment soft tissue following introduction (e.g. via injection, transplantation, or implantation) into a site of soft tissue. Also provided are methods of isolating muscle-derived progenitor cells, and methods of genetically modifying the cells for gene transfer therapy. The invention further provides methods of using compositions comprising muscle-derived progenitor cells for the augmentation and bulking of mammalian, including human, soft tissues in the treatment of various cosmetic or functional conditions, including malformation, injury, weakness, disease, or dysfunction. In particular, the present invention provides treatments and amelioration for dermatological conditions, gastroesophageal reflux, vesico-ureteral reflux, urinary incontinence, fecal incontinence, heart failure, and myocardial infarction.

10 Claims, 19 Drawing Sheets

OTHER PUBLICATIONS

Deasy et al., Current Opinion in Molecular Therapeutics, 4:382-389, 2002.*

Newman et al., Am. J. Nurs. 103:46-55, 2003.*

Jung et al., The Journal of Urology, 162:204-212, 1999.*

Huard et al., Gene Therapy 9:1617-1626, 2002.*

Arcila et al., J. Neurobiol 33:185-198, 1997.*

TA Rando et al., 1994, "Primary mouse myoblast purification, characterization, and transplantation for cell-mediated gene therapy", Journal of Cell Biology, 125:1275-1287.

Z. Qu et al., 1998, "Development of approaches to improve cell survival in myoblast transfer therapy", Journal of Cell Biology, 142:1257-1267.

J. Huard et al., 1992, "Human myoblast transplantation: preliminary results of 4 cases", Muscle and Nerve, 15:550-560.

CS Day et al., 1997, "Myoblast-mediated gene transfer to the joint", Journal of Orthopedic Research, 15:894-903.

G. Acsadi et al., 1994, "A differential efficiency of adenovirus-mediated in vivo gene transfer into skeletal muscle cells of different maturity", Human Molecular Genetics, 3:579-584.

C. Kasemkijwattana et al., 1998, "Development of approaches to improve the healing following muscle contusion", Cell Transplantation, 7:585-598.

KP Spindler et al., 1995, "Regional mitotic response of the meniscus to platelet-derived growth factor (PDGF-AB)", Journal of Orthopedic Research, 13:201-207.

E. Gussoni et al., 1992, "Normal dystrophin transcripts detected in Duchenne muscular dystrophy patients after myoblast transplantation", Nature, 356:435-438.

G, Karpati et al., 1993, "Myoblast transfer in Duchenne Muscular Dystrophy", Annals of Neurology, 34:8-17.

J.P. Tremblay et al., 1993, "Results of a triple blind clinical study of myoblast transplantations without immunosuppressive treatment in young boys with Duchenne muscular dystrophy", Cell Transplantation, 2:99-112.

J. Huard et al., 1994, "High efficiency of muscle regeneration after human myoblast clone transplantation in SCID mice", Journal of Clinical Investigation, 93:586-599.

J. Huard et al., 1994, "Human myoblast transplantation in immunodeficient and immunosuppressed mice: evidence of rejection", Muscle and Nerve 17:224-234.

J. Huard et al., 1995, "The route of administration is a major determinant of the transduction efficiency of rat tissues by adenoviral recombinants", Gene Therapy, 2:107-115.

M. Reza Dana et al., "Interleukin-1 Receptor Antagonist Suppresses Langerhans Cell Activity and Promotes Ocular Immune Privilege", *Investigative Ophthalmology & Visual Science*, 1998, 39:70-77.

G. Ferrari et al., "Muscle Regeneration by Bone Marrow-Derived Myogenic Progenitors", *Science*, 1998, 279:1528-1530.

E. Barr and J. Leiden, "Systemic Delivery of Recombinant Proteins by Genetically Modified Myoblasts", *Science*, 1991, 254:1507-1509.

T. Katagiri et al., "Bone Morphogenetic Protein-2 Converts the Differentiation Pathway of C2C12 Myoblasts into the Osteoblast Lineage", *J. Cell Biology*, 1994, 127:1755-1766.

T.A. Rando and H. Blau, "Primary Mouse Myoblast Purification, Characterization, and Transplantation for Cell-mediated Gene Therapy", *J. Cell Biology*, 1994, 125:1275-1287.

T. Yokoyama et al., "Gene Therapy as a Potential Treatment for BPH; Injection of Myoblast-Adenovirus Transfected with Human Inductible Nitric Oxide Synthase (iNOS) into the Proximal Urethra", *J. Urology*, 1999, 161 (4) Supplement:305 (Abstract 1175).

J. Huard et al., "Myoblast Injection into the Bladder Wall: A Possible Method of Modulating Detrusor Contractility and Cell-Mediated Gene Therapy for Bladder Dysfunction", *J. Urology*, 1998, 159 (5) Supplement:16 (Abstract 62).

J. Huard et al., "Nitric Oxide Synthase (NOS) Gene Therapy for Erectile Dysfunction; Comparison Between Plasmid, Adenovirus and Adenovirus Transduced Myoblast Vectors", *J. Urology*, 1998, 159:90 (Abstract 342).

K.A. Jackson et al., 1999, "Hematopoietic potential of stem cells isolated from murine skeletal muscle", PNAS, vol. 96, 25:14482-14486.

E. Gussoni et al., 1999, "Dystrophin expression in the mdx mouse restored by stem cell transplantation", Nature, 401:390-394.

Z. Qu et al., 1998, "Development of Approaches to Improve Cell Survival in Myoblast Transfer Therapy", The Journal of Cell Biology, vol. 142, 5:1257-1267.

D.S. Musgrave et al., 1998, "Muscle-based tissue engineering for the musculoskeletal system", Gene Therapy & Molecular Biology, vol. 3:1-15.

N. Yoshida et al., 1998, "Cell heterogeneity upon myogenic differentiation: down-regulation of MyoD and Myf-5 generates 'reserve cells'", Journal of Cell Science, 111:769-779.

J.R. Beauchamp et al., 1999, "Dynamics of Myoblast Transplantation Reveal a Discrete Minority of Precursors with Stem Cell-like Properties as the Myogenic Source", The Journal of Cell Biology, vol. 144, 6:1113-1121.

P. Seale et al., 2000, "A New Look at the Origin, Function, and 'Stem Cell' Status of Muscle Satellite Cells", Developmental Biology, 218: 115-124.

J.G. Gross et al., 1999, "Muscle Precursor Cells Injected Into Irradiated mdx Mouse Muscle persist After Serial Injury", Muscle & Nerve, 22:174-185.

T.D. Alden et al., 1999, "*In Vivo* Endochondral Bone Formation Using a Bone Morphogenetic Protein 2 Adenoviral Vector", Human Gene Therapy, 10:2245-2253.

A. Baroffio et al., 1996, "Identification of self-renewing myoblasts in the progeny of single human muscle satellite cells", Differentiation, 60:47-57.

Abstract: V. Nurcombe et al., 1985, "Motoneuron Survival and Neuritic Outgrowth Promoted by Different Cell Types in Embryonic Muscle", Developmental Brain Research, 21: abstract only.

C. Richler et al., 1970, "The *in Vitro* Cultivation and Differentiation Capacities of Myogenic Cell Lines", Developmental Biology, 23:1-22.

G. Bandara et al., 1993, "Intraarticular expression of biologically active interleukin 1-receptor-antagonist protein by ex vivo gene transfer", Proc. Natl. Acad. Sci. USA, 90:10764-10768.

Qu Zhuqing et al., 1999, "Identification of Muscle-Derived Stem Cells", *Molec. Biol. of the Cell*, 10:246a.

Smith et al., 1997, "Stable Intregration of an MDX Skeletal Muscle Cell Line into Dystrophic (MDX) Skeletal Muscle: Evidence for Stem Cell Status", *Cell Growth and Differentiation*, 8(8):927-34.

Jankowski et al., 2001, "Flow Cytometric Characterization of Myogenic Cell Populations Obtained Via the Preplate Technique: Potential for Rapid Isolation of Muscle-derived Stem Cells", *Human Gene Therapy*, 12:619-28.

* cited by examiner x 40 x 100

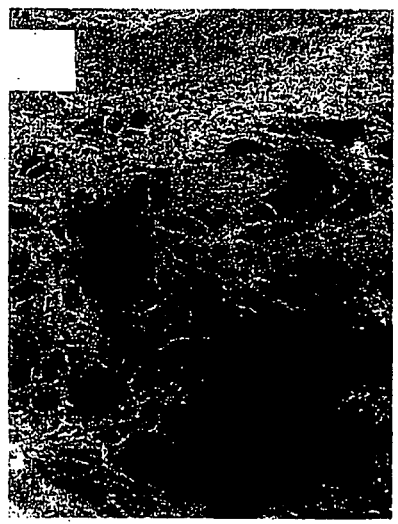
FIG. 5C
FIG. 5B
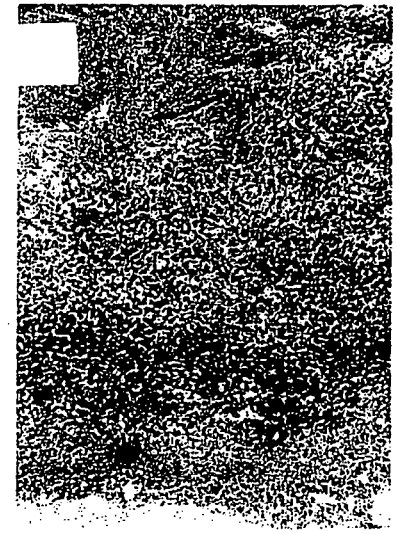
FIG. 5A
FIG. 5F
FIG. 5E
FIG. 5D

PP1-4

PP6

PP1-4                             PP6
 
FIG. 11D                     FIG. 11J
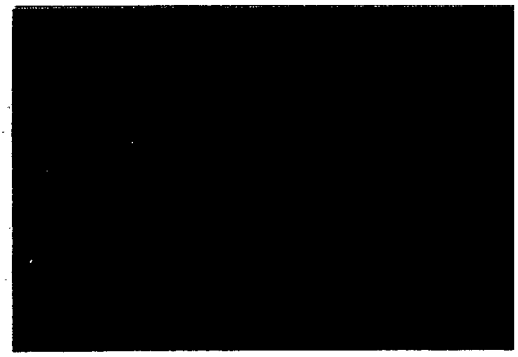 
FIG. 11E                     FIG. 11K
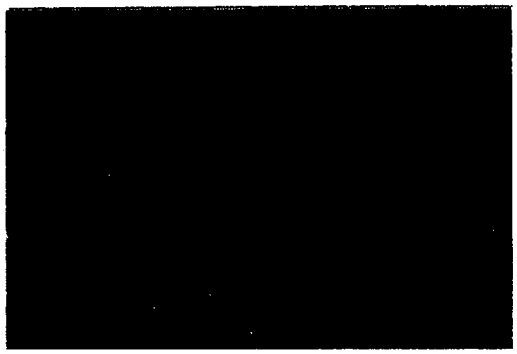 
FIG. 11F                     FIG. 11L

 
FIG. 14A  FIG. 14B
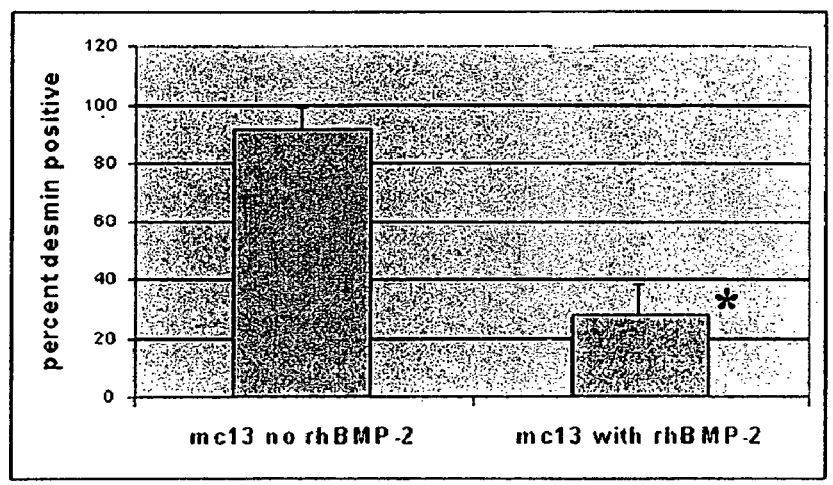
FIG. 14C
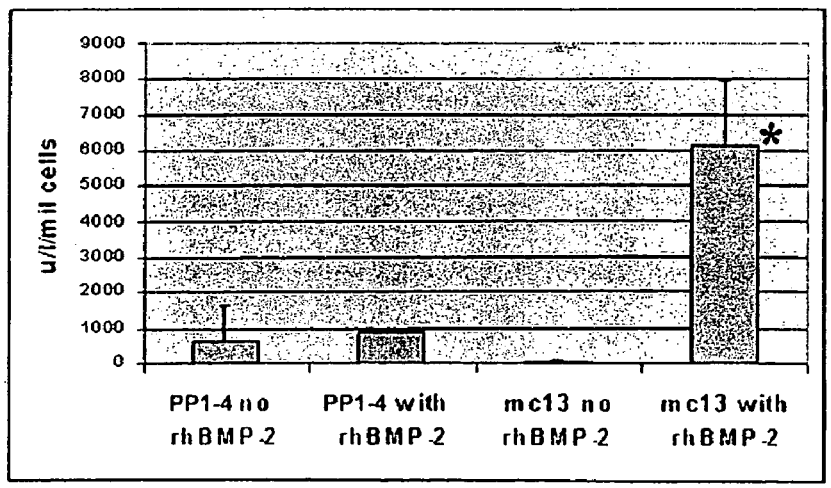
FIG. 14D

 
FIG. 15A  FIG. 15B
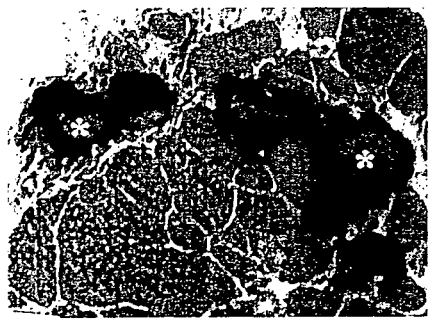 
FIG. 15C  FIG. 15D
 
FIG. 15E  FIG. 15F

 
FIG. 16A  FIG. 16B
 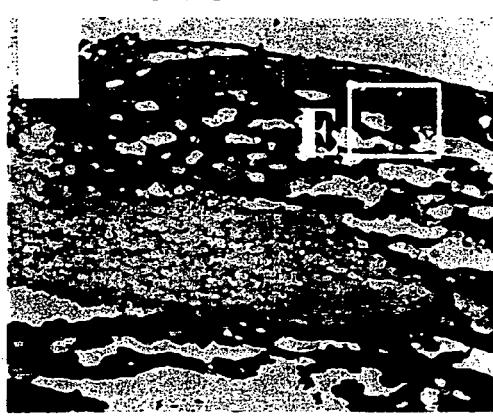
FIG. 16C  FIG. 16D
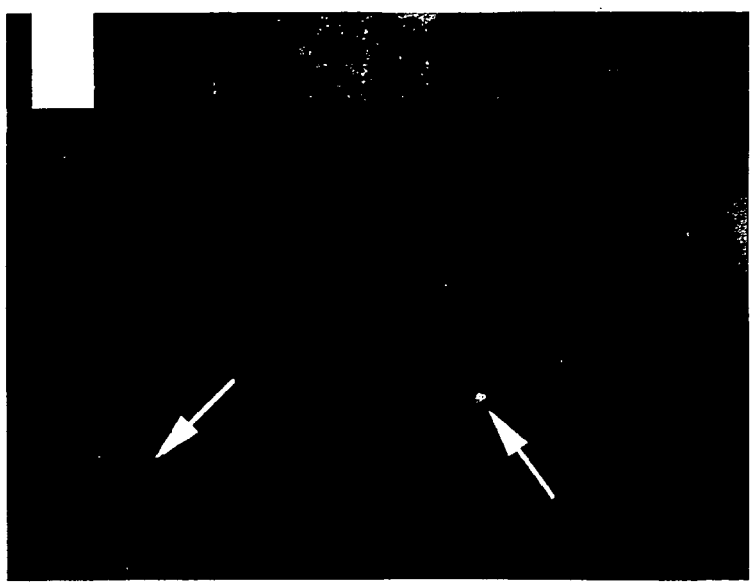
FIG. 16E

SEQUENCE LISTING

```
<160> NUMBER OF SEQ ID NOS:  12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:CD34 UP
      oligonucleotide sequence

<400> SEQUENCE: 1
taacttgact tctgctacca                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:CD34 DOWN
      oligonucleotide sequence

<400> SEQUENCE: 2
gtggtcttac tgctgtcctg                                               20

<210> SEQ ID NO 3
<211> LENGTH: 20
<212> TYPE: DNA
<213> ORGANISM: Artificial Sequence
```

```
<220> FEATURE:
<223> OTHER INFORMATION: Description of Artificial Sequence:C-MET UP
      oligonucleotide sequence

<400> SEQUENCE: 3
gaatgtcgtc ctacacggcc                                                    20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:C-MET DOWN
      oligonucleotide sequence

<400> SEQUENCE: 4
cactacacag tcaggacact gc                                                 22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:MNF UP
      oligonucleotide sequence

<400> SEQUENCE: 5
tacttcatca aagtccctcg gtc                                                23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:MNF DOWN
      oligonucleotide sequence

<400> SEQUENCE: 6
gtactctgga acagaggcta actt                                               24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:BCL-2 UP
      oligonucleotide sequence

<400> SEQUENCE: 7
agccctgtgc caccatgtgt c                                                  21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:BCL-2 DOWN
      oligonucleotide sequence

<400> SEQUENCE: 8
ggcaggtttg tcgacctcac t                                                  21

<210> SEQ ID NO 9
<211> LENGTH: 24
<212> TYPE: DNA
<213> ORGANISM: Artificial Sequence
<220> FEATURE:
```

-continued

```
<223> OTHER INFORMATION: Description of Artificial Sequence:MYOGENIN UP
      oligonucleotide sequence

<400> SEQUENCE: 9
caaccaggag gagcgcgatc tccg                                              24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:MYOGENIN
      DOWN oligonucleotide sequence

<400> SEQUENCE: 10
aggcgctgtg ggagttgcat tcact                                             25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:MYOD UP
      oligonucleotide sequence

<400> SEQUENCE: 11
gctctgatgg catgatggat tacagcg                                           27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:MYOD DOWN
      oligonucleotide sequence

<400> SEQUENCE: 12
atgctggaca ggcagtcgag gc                                                22
```

SOFT TISSUE AND BONE AUGMENTATION AND BULKING UTILIZING MUSCLE-DERIVED PROGENITO COMPOSITIONS, AND TREATMENTS THEREOF

This application is a continuation-in-part of patent application Ser. No. 09/302,896, filed Apr. 30, 1999, now U.S. Pat. No. 6,866,842, issued Mar. 15, 2005, which claims benefit of provisional patent application U.S. Ser. No. 60/083,917, filed May 1, 1998.

FIELD OF THE INVENTION

The present invention relates to muscle-derived progenitor cells (MDC) and compositions of MDC and their use in the augmentation of body tissues, particularly soft tissue and bone. In particular, the present invention relates to muscle-derived progenitor cells that show long-term survival following introduction into soft tissues and bone, methods of isolating MDC, and methods of using MDC-containing compositions for the augmentation of human or animal soft tissues and bone, including epithelial, adipose, nerve, organ, muscle, ligament, and cartilage tissue. The invention also relates to novel uses of muscle-derived progenitor cells for the treatment of cosmetic or functional conditions, such as dermatological conditions, gastroesophageal reflux, vesicoureteral reflux, urinary incontinence, fecal incontinence, skeletal muscle weakness, heart failure, and injury or weakness associated with myocardial infarction.

BACKGROUND OF THE INVENTION

Augmentation of soft tissue using synthetic materials such as silicone or polytetrafluoroethylene (PTFE) is well known in the art. U.S. Pat. No. 5,876,447 to Arnett discloses the use of silicone implants for facial plastic surgery. However, such synthetic materials are foreign to the host tissue, and cause an immunological response resulting in the encapsulation of the implant and scarring of the surrounding tissues. Thus, the implant may produce additional functional or aesthetic problems.

Soft tissue augmentation using biopolymers such as collagen or hyaluronic acid has also been described. For example, U.S. Pat. No. 4,424,208 to Wallace et al. discloses methods of augmenting soft tissue utilizing collagen implant material. In addition, U.S. Pat. No. 4,965,353 to della Valle et al. discloses esters of hyaluronic acid that can be used in cosmetic surgery. However, these biopolymers are also foreign to the host tissue, and cause an immunological response resulting in the reabsorption of the injected material. Biopolymers are therefore unable to provide long-term tissue augmentation. Overall, the use of biopolymers or synthetic materials has been wholly unsatisfactory for the purpose of augmenting soft tissue.

Soft tissue augmentation using cell-based compositions has also been developed. U.S. Pat. No. 5,858,390 to Boss, Jr. discloses the use of autologous dermal fibroblasts for the treatment of cosmetic and aesthetic skin defects. Although this treatment avoids the problems inherent in the implantation or injection of synthetic materials or biopolymers, it results in other complications. Because fibroblasts produce collagen, the cells can cause the stiffening and distortion of the tissues surrounding the implant site.

The use of autologous fat cells as an injectable bulking agent has also been described (For review, see K. Mak et al., 1994, *Otolaryngol. Clin. North. Am.* 27:211–22; American Society of Plastic and Reconstructive Surgery: Report on autologous fat transplantation by the ad hoc committee on new procedures, 1987, *Chicago: American Society of Plastic and Reconstructive Surgery*; A. Chaichir et al., 1989, *Plast. Reconstr. Surg.* 84: 921–935; R. A. Ersek, 1991, *Plast. Reconstr. Surg.* 87:219–228; H. W. Horl et al., 1991, *Ann. Plast. Surg.* 26:248–258; A. Nguyen et al., 1990, *Plast. Reconstr. Surg.* 85:378–389; J. Sartynski et al., 1990, *Otolaryngol. Head Neck Surg.* 102:314–321. However, the fat grafting procedure provides only temporary augmentation, as injected fat is reabsorbed into the host. In addition, fat grafting can result in nodule formation and tissue asymmetry.

Myoblasts, the precursors of muscle fibers, are mononucleated muscle cells that fuse to form post-mitotic multinucleated myotubes, which can provide long-term expression and delivery of bioactive proteins (T. A. Partridge and K. E. Davies, 1995, *Brit. Med. Bulletin* 51:123–137; J. Dhawan et al., 1992, *Science* 254: 1509–12; A. D. Grinnell, 1994, *Myology* Ed 2, A. G. Engel and C. F. Armstrong, McGraw-Hill, Inc., 303–304; S. Jiao and J. A. Wolff, 1992, *Brain Research* 575:143–7; H. Vandenburgh, 1996, *Human Gene Therapy* 7:2195–2200).

Cultured myoblasts contain a subpopulation of cells that show some of the self-renewal properties of stem cells (A. Baroffio et al., 1996, *Differentiation* 60:47–57). Such cells fail to fuse to form myotubes, and do not divide unless cultured separately (A. Baroffio et al., supra). Studies of myoblast transplantation (see below) have shown that the majority of transplanted cells quickly die, while a minority survive and mediate new muscle formation (J. R. Beuchamp et al., 1999, *J. Cell Biol.* 144:1113–1122). This minority of cells shows distinctive behavior, including slow growth in tissue culture and rapid growth following transplantation, suggesting that these cells may represent myoblast stem cells (J. R. Beuchamp et al., supra).

Myoblasts have been used as vehicles for gene therapy in the treatment of various muscle- and non-muscle-related disorders. For example, transplantation of genetically modified or unmodified myoblasts has been used for the treatment of Duchenne muscular dystrophy (E. Gussoni et al., 1992, *Nature,* 356:435–8; J. Huard et al., 1992, *Muscle & Nerve,* 15:550–60; G. Karpati et al., 1993, *Ann. Neurol.,* 34:8–17; J. P. Tremblay et al., 1993, *Cell Transplantation,* 2:99–112; P. A. Moisset et al., 1998, *Biochem. Biophys. Res. Commun.* 247:94–9; P. A. Moisset et al., 1998, *Gene Ther.* 5:1340–46). In addition, myoblasts have been genetically engineered- to produce proinsulin for the treatment of Type 1 diabetes (L. Gros et al., 1999, *Hum. Gen. Ther.* 10:1207–17); Factor IX for the treatment of hemophilia B (M. Roman et al., 1992, *Somat. Cell. Mol. Genet.* 18:247–58; S. N. Yao et al., 1994, *Gen. Ther.* 1:99–107; J. M. Wang et al., 1997, *Blood* 90:1075–82; G. Hortelano et al., 1999, *Hum. Gene Ther.* 10:1281–8); adenosine deaminase for the treatment of adenosine deaminase deficiency syndrome (C. M. Lynch et al., 1992, *Proc. Natl. Acad. Sci. USA,* 89:1138–42); erythropoietin for the treatment of chronic anemia (E. Regulier et al., 1998, *Gene Ther.* 5:1014–22; B. Dalle et al., 1999, *Gene Ther.* 6:157–61), and human growth hormone for the treatment of growth retardation (K. Anwer et al., 1998, *Hum. Gen. Ther.* 9:659–70).

Myoblasts have also been used to treat muscle tissue damage or disease, as disclosed in U.S. Pat. No. 5,130,141 to Law et al., U.S. Pat. No. 5,538,722 to Blau et al., and application U.S. Ser. No. 09/302,896 filed Apr. 30, 1999 by Chancellor et al. In addition, myoblast transplantation has been employed for the repair of myocardial dysfunction (C.

E. Murry et al., 1996, *J. Clin. Invest.* 98:2512–23; B. Z. Atkins et al., 1999, *Ann. Thorac. Surg.* 67:124–129; B. Z. Atkins et al., 1999, *J. Heart Lung Transplant.* 18:1173–80).

In spite of the above, in most cases, primary myoblast-derived treatments have been associated with low survival rates of the cells following transplantation due to migration and/or phagocytosis. To circumvent this problem, U.S. Pat. No. 5,667,778 to Atala discloses the use of myoblasts suspended in a liquid polymer, such as alginate. The polymer solution acts as a matrix to prevent the myoblasts from migrating and/or undergoing phagocytosis after injection. However, the polymer solution presents the same problems as the biopolymers discussed above. Furthermore, the Atala patent is limited to uses of myoblasts in only muscle tissue, but no other tissue.

Thus, there is a need for other, different soft tissue augmentation materials that are long-lasting, compatible with a wide range of host tissues, and which cause minimal inflammation, scarring, and/or stiffening of the tissues surrounding the implant site. Accordingly, the muscle-derived progenitor cell-containing compositions of the present invention are provided as improved and novel materials for augmenting soft tissues. Further provided are methods of producing muscle-derived progenitor cell compositions that show long-term survival following transplantation, and methods of utilizing MDC and compositions containing MDC to treat various aesthetic and/or functional defects, including, for example, dermatological conditions or injury, and muscle weakness, injury, disease, or dysfunction.

It is notable that prior attempts to use myoblasts for non-muscle soft tissue augmentation were unsuccessful (U.S. Pat. No. 5,667,778 to Atala). Therefore, the findings disclosed herein are unexpected, as they show that the muscle-derived progenitor cells according to the present invention can be successfully transplanted into non-muscle and muscle soft tissue, including epithelial tissue, and exhibit long-term survival. As a result, MDC and compositions comprising MDC can be used as a general augmentation material for muscle or non-muscle soft tissue augmentation, as well as for bone production. Moreover, since the muscle-derived progenitor cells and compositions of the present invention can be derived from autologous sources, they carry a reduced risk of immunological complications in the host, including the reabsorption of augmentation materials, and the inflammation and/or scarring of the tissues surrounding the implant site.

Although mesenchymal stem cells can be found in various connective tissues of the body including muscle, bone, cartilage, etc. (H. E. Young et al., 1993, *In Vitro Cell Dev. Biol.* 29A:723–736; H. E. Young, et al., 1995, *Dev. Dynam.* 202:137–144), the term mesenchymal has been used historically to refer to a class of stem cells purified from bone marrow, and not from muscle. Thus, mesenchymal stem cells are distinguished from the muscle-derived progenitor cells of the present invention. Moreover, mesenchymal cells do not express the CD34 cell marker (M. F. Pittenger et al, 1999, *Science* 284:143–147), which is expressed by the muscle-derived progenitor cells described herein.

SUMMARY OF THE INVENTION

It is an object of the present invention to provide novel muscle-derived progenitor cells (MDC) and MDC compositions exhibiting long-term survival following transplantation. The MDC of this invention and compositions containing the MDC comprise early progenitor muscle cells, i.e., muscle-derived stem cells, that express progenitor cell markers, such as desmin, M-cadherin, MyoD, myogenin, CD34, and Bcl-2. In addition, these early progenitor muscle cells express the Flk-1, Sca-1, MNF, and c-met cell markers, but do not express the CD45 or c-Kit cell markers.

It is another object of the present invention to provide methods for isolating and enriching muscle-derived progenitor cells from a starting muscle cell population. These methods result in the enrichment of MDC that have long-term survivability after transplantation or introduction into a site of soft tissue. The MDC population according to the present invention is particularly enriched with cells that express progenitor cell markers, such as desmin, M-cadherin, MyoD, myogenin, CD34, and Bcl-2. This MDC population also expresses the Flk-1, Sca-1, MNF, and c-met cell markers, but does not express the CD45 or c-Kit cell markers.

It is yet another object of the present invention to provide methods of using MDC and compositions comprising MDC for the augmentation of muscle soft tissue, or non-muscle soft tissue, including skin, blood vessels, adipose, nerve, skeletal muscle, smooth muscle, ligament, cartilage, and various organ tissues, without the need for polymer carriers or special culture media for transplantation. Such methods include the administration of MDC compositions by introduction into soft tissue, for example by direct injection into tissue, or by systemic distribution of the compositions. Preferably, soft tissue includes non-bone body tissues. More preferably, soft tissue includes non-striated muscle, non-bone body tissues. Most preferably, soft tissue includes non-muscle, non-bone body tissues. As used herein, augmentation refers to filling, bulking, supporting, enlarging, extending, or increasing the size or mass of body tissue.

It is another object of the present invention to provide MDC-based treatments for a) cosmetic or aesthetic conditions; b) gastroesophageal reflux symptoms and conditions; c) fecal and urinary incontinence; and d) skeletal and smooth muscle weakness, injury, disease, or dysfunction.

It is yet another object of the present invention to provide methods of augmenting bone or soft tissue, either muscle-derived soft tissue, or non-muscle-derived soft tissue, following injury, wounding, surgeries, traumas, non-traumas, or other procedures that result in fissures, openings, depressions, wounds, and the like, in the skin or in internal soft tissues or organs.

It is a further object of the present invention to provide MDC and compositions comprising MDC that are modified through the use of chemicals, growth media, and/or genetic manipulation. Such MDC and compositions thereof comprise chemically or genetically modified cells useful for the production and delivery of biological compounds, and the treatment of various diseases, conditions, injuries, or illnesses.

Additional objects and advantages afforded by the present invention will be apparent from the detailed description and exemplification hereinbelow.

DESCRIPTION OF THE FIGURES

The patent or patent application file contains at least one photographic reproduction executed in color. Copies of this patent or patent application with color photographic reproduction(s) will be provided by the U.S. Patent and Trademark Office upon request and payment of the necessary fee.

The appended drawings of the figures are presented to further describe the invention and to assist in its understanding through clarification of its various aspects.

FIGS. 1A–1F show Trichrome staining at 40× magnification following injection of either collagen or MDC into skin. At 5 days, 2 weeks, or 4 weeks post-injection, tissue samples were obtained and prepared for analysis. FIGS. 1A and 1D show the results of MDC versus collagen injection into the skin at 5 days post-injection; FIGS. 1B and 1E show the results at 2 weeks post-injection; and FIGS. 1C and 1F show the results at 4 weeks post-injection. Arrowheads in FIGS. 1D–1F indicate the presence of MDC in the injected areas (deep pink color). FIGS. 1A–1F demonstrate that following injection into the subcutaneous space, MDC persisted and maintained/augmented the abdominal wall subcutaneous tissue for up to at least 4 weeks, while collagen did not persist by 2 weeks post-injection into the skin. (Example 3).

FIG. 2A shows injected tissues at 100× magnification; FIG. 2B shows injected tissues at 40× magnification. FIGS. 2A and 2B demonstrates that MDC injections maintained the lower esophageal sphincter and anal sphincter soft tissue augmentation for up to 3 days following injection FIG. 3A shows injected tissues at low (40×) magnification; FIG. 3B shows injected tissues at high (100×) magnification. FIGS. 3A and 3B demonstrate that MDC injections maintained the bladder-ureteral junction soft tissue augmentation for up to 3 days following injection FIG. 4A shows untreated cryodamaged bladder tissue. FIG. 4B shows cryodamaged bladder tissue treated with MDC injections; MDC are indicated by β-galactosidase staining. FIGS. 4A and 4B demonstrate that MDC injections maintained the soft tissue augmentation of the cryodamaged bladder tissue for up to 30 days following injection.

FIGS. 5A–5I illustrate cellular differentiation of MDC following injection into cryodamaged bladder tissue. Injections were made into the bladder wall at the site of cryoinjury, and tissue samples were obtained and prepared for analysis at 5, 35, or 70 days post-injection. Injected MDC are shown by staining for α-galactosidase, and undifferentiated MDC are shown by α-smooth muscle actin (α-SM actin) staining. MDC that have differentiated into myotubes or myofibers are shown by fast myosin heavy chain (fast MyHC) staining. Arrows show fast MyHC. At day 5 post-injection, multiple MDC are observed at the injection area and only some MDC have differentiated into myotubes, as shown by the high levels of β-galactosidase (FIG. 5A) and α-SM actin (FIG. 5D) staining, and the relatively low levels of Fast MyHC (FIG. 5G) staining. At day 35 post-injection, multiple MDC are observed at the injection area, and many have differentiated into myotubes, as shown by the high levels of β-galactosidase staining (FIG. 5B), the decrease in α-SM actin (FIG. 5E) staining; and the increase in Fast MyHC (FIG. 5H) staining. At day 70 post-injection, MDC are observed at the injection area, and almost all MDC have differentiated into myofibers, as shown by the high levels of β-galactosidase (FIG. 5C), the decrease in α-SM actin (FIG. 5F) staining, and the high levels of Fast MyHC (FIG. 5I) staining. Magnification is 200×. FIGS. 5A–5I demonstrate that MDC remain viable and begin differentiation for up to 70 days following injection into bladder soft tissue.

FIGS. 6A–6C show injected tissue at high (200×) magnification. FIGS. 6A–6D demonstrate that MDC induce innervation for up to 6 months following injection into cryodamaged bladder tissues.

FIG. 7A shows injected tissue at low (100×) magnification; FIG. 7B shows injected tissue at high (200×) magnification.

FIG. 8A shows low (100×) magnification; FIG. 8B shows high (200×) magnification.

FIG. 9A shows injected tissues viewed by low (100×) magnification; FIG. 9B shows injected tissues viewed by high (200×) magnification.

FIG. 10A shows injected tissues viewed by low (100×) magnification; FIG. 10B shows injected tissues viewed by high (200×) magnification. FIGS. 7A–7B, 8A–8B, 9A–9B, and 10A–10B demonstrate that MDC remain viable following injection into a variety of different tissue types without damaging the host tissues.

FIGS. 11A–11L illustrate immunohistochemical analysis of PP1–4 and PP6 cell populations from mdx mice showing expression of cell markers including desmin, MyoD, and myogenin (markers specific for myogenic lineages), M-cadherin (satellite cell specific marker), Bcl-2 (early myogenesis marker), CD34 (hematopoietic or stromal cell marker). FIGS. 11A–11L demonstrate that PP14 and PP6 cell populations show comparable percentage of cells expressing desmin (FIGS. 11A and 11G), MyoD (FIGS. 11E and 11K), and myogenin (FIGS. 11F and 11L), while the PP6 population shows a lower percentage of cells expressing M-cadherin (FIGS. 11D and 11J), but a higher percentage of cells expressing Bcl-2 (FIGS. 11C and 11I) and CD34 (FIGS. 11B and 11H), compared with the PP1–4 population.

FIG. 12A shows normal mouse muscle cells (see arrow) and vascular endothelial cells (see arrowhead) stained with anti-CD34 antibodies and visualized by fluorescence microscopy. FIG. 12B shows the same cells co-stained with desmin and collagen type IV antibodies. FIG. 12C shows the same cells co-stained with Hoechst to show the nuclei. FIG. 12D shows a composite of the cells co-stained for CD34, desmin, collagen type IV, and Hoechst. FIG. 12E shows normal mouse muscle cells (see arrow) stained with anti-Bcl-2 antibodies and visualized by fluorescence microscopy. FIG. 12F shows the same cells co-stained with desmin and collagen type IV antibodies. FIG. 12G shows the same cells co-stained with Hoechst to show the nuclei. FIG. 12H shows a composite of the cells co-stained for CD34, desmin, collagen type IV, and Hoechst. FIG. 12I shows satellite cells stained with anti-M-cadherin antibodies (see arrow). Cells were viewed at 40× magnification. FIGS. 12A–12D demonstrate the co-localization of CD34 and desmin, while FIGS. 12E–12H demonstrate the co-localization of Bcl-2 and desmin.

FIG. 13A shows cells grown to >50% cell confluency in the absence of rhBMP-2. FIG. 13B shows cells grown to >50% cell confluency in the presence of 200 ng/ml rhBMP-2. FIG. 13C shows cells grown to >90% cell confluency in the absence of rhBMP-2. FIG. 13D shows cells grown to >90% confluency in the presence of 200 ng/ml rhBMP-2. FIG. 13E shows cells stained for osteocalcin expression (osteoblast cell marker; see arrows). Cells were viewed at 10× magnification. FIGS. 13A–13E demonstrate that mc13 cells are capable of differentiating into osteoblasts upon exposure to rhBMP-2.

FIGS. 14A–14D illustrate the effects on the percentage of mc13 cells expressing desmin and alkaline phosphatase in response to rhBMP-2 treatment. FIG. 14A shows desmin staining of newly isolated mc13 clones. FIG. 14B shows a phase contrast view of the same cells. FIG. 14C shows the levels of desmin staining in mc13 cells following 6 days of incubation in growth media with or without 200 ng/ml rhBMP-2. FIG. 14D shows the levels of alkaline phosphate staining in PP1–4 cells and mc13 cells following 6 days of incubation in growth media with or without 200 ng/ml rhBMP-2. * indicates a statistically significant result (student's t-test). FIG. 14C demonstrates that a decreasing number of mc13 cells express desmin in the presence of rhBMP-2, while FIG. 14D demonstrates that an increasing number of mc13 cells express alkaline phosphatase in the presence of rhBMP-2, suggesting decreasing myogenic characteristics and increasing osteogenic characteristics of the cells in the presence of rhBMP-2.

FIGS. 15A–15G illustrate the in vivo differentiation of mc13 cells into myogenic and osteogenic lineages. Mc13 cells were stably transfected with a construct containing LacZ and the dystrophin gene, and introduced by intramuscular or intravenous injection into hind limbs of mdx mice. After 15 days, the animals were sacrificed and the hind limb musculature was isolated for histology. FIG. 15A shows mc13 cells at the intramuscular injection site stained for LacZ. FIG. 15B shows the same cells co-stained for dystrophin. FIG. 15C shows mc13 cells in the region of the intravenous injection stained for LacZ. FIG. 15D shows the same cells co-stained for dystrophin. In a separate experiment, mc13 cells were transduced with adBMP-2, and 0.5–1.0×10$^6$ cells were injected into hind limbs of SCID mice. After 14 days, the animals were sacrificed, and the hind limb muscle tissues were analyzed. FIG. 15E shows radiographic analysis of the hind limb to determine bone formation. FIG. 15F shows the cells derived from the hind limb stained for LacZ. FIG. 15G shows cells stained for dystrophin. FIGS. 15A–15D demonstrate that mc13 cells can rescue dystrophin expression via intramuscular or intravenous delivery. FIGS. 15E–15G demonstrate that mc13 cells are involved in ectopic bone formation. Cells were viewed at the following magnifications: 40× (FIGS. 15A–15D), 10× (FIGS. 15F–15G)

FIGS. 16A–16E illustrate the enhancement of bone healing by rhBMP-2 producing primary muscle cells. A 5 mm skull defect was created in female SCID mice using a dental burr, and the defect was filled with a collagen sponge seeded with mc13 cells with or without adBMP-2. The animals were sacrificed at 14 days, inspected, and analyzed microscopically for indications of bone healing. FIG. 16A shows a skull treated with mc13 cells without adBMP-2. FIG. 16B shows a skull treated with mc13 cells transduced with adBMP-2. FIG. 16C shows a histological sample of the skull treated with mc13 cells without adBMP-2 analyzed by von Kossa staining. FIG. 16D shows a histological sample of the skull treated with mc13 cells transduced with adBMP-2 analyzed by von Kossa staining. FIG. 16E shows a histological sample of the skull treated with the mc13 cells transduced with adBMP-2 analyzed by hybridization with a Y-chromosome specific probe to identify the injected cells (green fluorescence shown by arrows), and stained with ethidium bromide to identify the nuclei (indicated by red fluorescence). FIGS. 16A–16E demonstrate that mc13 cells expressing rhBMP-2 can contribute to the healing of bone defects.

DETAILED DESCRIPTION OF THE INVENTION

Muscle-Derived Cells and Compositions

Figure 1A:
FIGS. 1A–1F illustrate the results of soft tissue augmentation utilizing injections of MDC compositions compared with injection of conventional bovine collagen. For FIGS. 1A–1F, either MDC (FIGS. 1D–1F) or collagen (1A–1C) were injected into the skin of the abdominal wall. The area of injection was the interface of the dermis and the subcutaneous connective tissue which is the skin.

The present invention provides MDC comprised of early progenitor cells (also termed muscle-derived progenitor cells or muscle-derived stem cells herein) that show long-term survival rates following transplantation into body tissues, preferably soft tissues. To obtain the MDC of this invention, a muscle explant, preferably skeletal muscle, is obtained from an animal donor, preferably from a mammal, including humans. This explant serves as a structural and functional syncytium including "rests" of muscle precursor cells (T. A. Partridge et al., 1978, Nature 73:306–8; B. H. Lipton et al., 1979, Science 205:12924).

Cells isolated from primary muscle tissue contain mixture of fibroblasts, myoblasts, adipocytes, hematopoietic, and muscle-derived progenitor cells. The progenitor cells of a muscle-derived population can be enriched using differential adherence characteristics of primary muscle cells on collagen coated tissue flasks, such as described in U.S. Pat. No. 6,866,842 of Chancellor et al. Cells that are slow to adhere tend to be morphologically round, express high levels of desmin, and have the ability to fuse and differentiate into multinucleated myotubes U.S. Pat. No. 6,866,842 of Chancellor et al.). A subpopulation of these cells was shown to respond to recombinant human bone morphogenic protein 2 (rhBMP-2) in vitro by expressing increased levels of alkaline phosphatase, parathyroid hormone dependent 3',5'-cAMP, and osteogenic lineage and myogenic lineages (U.S. Pat. No. 6,866,842 of Chancellor et al.; T. Katagiri et al., 1994, *J. Cell Biol.*, 127:1755–1766).

In accordance with the present invention, populations of rapidly adhering MDC (PP1–4) and slowly adhering, round MDC (PP6) were isolated and enriched from skeletal muscle explants and tested for the expression of various markers using immunohistochemistry to determine the presence of pluripotent cells among the slowly adhering cells (Example 1; patent application U.S. Ser. No. 09/302,896 of Chancellor et al.). As shown in Table 3, Example 9 herein, the PP6 cells expressed myogenic markers, including desmin, MyoD, and Myogenin. The PP6 cells also expressed c-met and MNF, two genes which are expressed at an early stage of myogenesis (J. B. Miller et al., 1999, *Curr. Top. Dev. Biol.* 43:191–219; see Table 3). The PP6 showed a lower percentage of cells expressing M-cadherin, a satellite cell-specific marker (A. Irintchev et al., 1994, *Development Dynamics* 199:326–337), but a higher percentage of cells expressing Bcl-2, a marker limited to cells in the early stages of myogenesis (J. A. Dominov et al., 1998, *J. Cell Biol.* 142:537–544). The PP6 cells also expressed CD34, a marker identified with human hematopoietic progenitor cells, as well as stromal cell precursors in bone marrow (R. G. Andrews et al., 1986, *Blood* 67:842–845; C. I. Civin et al., 1984, *J. Immunol.* 133:157–165; L. Fina et al, 1990, *Blood* 75:2417–2426; P. J. Simmons et al., 1991, *Blood* 78:2848–2853; see Table 3). The PP6 cells also expressed Flk-1, a mouse homologue of human KDR gene which was recently identified as a marker of hematopoietic cells with stem cell-like characteristics (B. L. Ziegler et al., 1999, *Science* 285:1553–1558; see Table 3). Similarly, the PP6 cells expressed Sca-1, a marker present in hematopoietic cells with stem cell-like characteristics (M. van de Rijn et al., 1989, *Proc. Natl. Acad. Sci. USA* 86:4634–8; M. Osawa et al., 1996, *J. Immunol.* 156:3207–14; see Table 3). However, the PP6 cells did not express the CD45 or c-Kit hematopoietic stem cell markers (reviewed in L K. Ashman, 1999, *Int. J. Biochem. Cell. Biol.* 31:1037–51; G. A. Koretzky, 1993, *FASEB J.* 7:420–426; see Table 3).

Preferred in the present invention is the PP6 population of muscle-derived progenitor cells having the characteristics described herein. These muscle-derived progenitor cells express the desmin, CD34, and Bcl-2 cell markers. In accordance with the present invention, the PP6 cells are isolated by the techniques described herein (Example 1) to obtain a population of muscle-derived progenitor cells that have long-term survivability following transplantation. The PP6 muscle-derived progenitor cell population comprises a significant percentage of cells that express progenitor cell markers such as desmin, CD34, and Bcl-2. In addition, PP6 cells express the Flk-1 and Sca-1 cell markers, but do not express the CD45 or c-Kit markers. Preferably, greater than 95% of the PP6 cells express the desmin, Sca-1, and Flk-1 markers, but do not express the CD45 or c-Kit markers. It is preferred that the PP6 cells are utilized within about 1 day or about 24 hours after the last plating.

As an alternative to the pre-plating method, the MDC of the present invention can be isolated by fluorescence-activated cell sorting (FACS) analysis using labeled antibodies against one or more of the cell surface markers expressed by the MDC (C. Webster et al., 1988, *Exp. Cell. Res.* 174: 252–65; J. R. Blanton et al., 1999, *Muscle Nerve* 22:43–50). For example, FACS analysis can be performed using labeled antibodies to directed to CD34, Flk-1, Sca-1, and/or other cell-surface markers described herein to select a population of PP6-like cells that exhibit long-term survivability when introduced into the host tissue. Also encompassed by the present invention is the use of one or more fluorescence-detection labels, for example, fluorescein or rhodamine, for antibody detection of different cell marker proteins.

Muscle-Derived Cell-Based Treatments

In one embodiment of the present invention, the MDC are isolated from a skeletal muscle source and introduced or transplanted into a muscle or non-muscle soft tissue site of interest, or into bone structures. Advantageously, the MDC of the present invention are isolated and enriched to contain a large number of progenitor cells showing long-term survival following transplantation. In addition, the muscle-derived progenitor cells of this invention express a number of characteristic cell markers, such desmin, CD34, and Bcl-2. Furthermore, the muscle-derived progenitor cells of this invention express the Sca-1, and Flk-1 cell markers, but do not express the CD45 or c-Kit cell markers (see Example 1).

MDC and compositions comprising MDC of the present invention can be used to repair, treat, or ameliorate various aesthetic or functional conditions (e.g. defects) through the augmentation of muscle or non-muscle soft tissues. In particular, such compositions can be used as soft-tissue bulking agents for the treatment of: 1) cosmetic and aesthetic conditions of the skin; 2) conditions of the lumen; 3) gastroesophageal reflux symptoms or conditions; 4) fecal incontinence; 5) skeletal muscle weakness, disease, injury or dysfunction; and 6) smooth muscle weakness, disease, injury, or dysfunction. In addition, such MDC and compositions thereof can be used for augmenting soft tissue not associated with injury by adding bulk to a soft tissue area, opening, depression, or void in the absence of disease or trauma, such as for "smoothing" or removing a wrinkle. Multiple and successive administrations of MDC are also embraced by the present invention.

For MDC-based treatments, a skeletal muscle explant is preferably obtained from an autologous or heterologous human or animal source. An autologous animal or human source is more preferred. MDC compositions are then prepared and isolated as described herein. To introduce or transplant the MDC and/or compositions comprising the MDC according to the present invention into a human or animal recipient, a suspension of mononucleated muscle cells is prepared. Such suspensions contain concentrations of the muscle-derived progenitor cells of the invention in a physiologically-acceptable carrier, excipient, or diluent. For example, suspensions of MDC for administering to a subject can comprise $10^8$ to $10^9$ cells/ml in a sterile solution of complete medium modified to contain the subject's serum, as an alternative to fetal bovine serum. Alternatively, MDC suspensions can be in serum-free, sterile solutions, such as cryopreservation solutions (Celox Laboratories, St. Paul, Minn.). The MDC suspensions can then be introduced e.g., via injection, into one or more sites of the donor tissue.

The described cells can be administered as a pharmaceutically or physiologically acceptable preparation or composition containing a physiologically acceptable carrier, excipient, or diluent, and administered to the tissues of the recipient organism of interest, including humans and non-human animals. The MDC-containing composition can be prepared by resuspending the cells in a suitable liquid or solution such as sterile physiological saline or other physiologically acceptable injectable aqueous liquids. The amounts of the components to be used in such compositions can be routinely determined by those having skill in the art.

The MDC or compositions thereof can be administered by placement of the MDC suspensions onto absorbent or adherent material, i.e., a collagen sponge matrix, and insertion of the MDC-containing material into or onto the site of interest. Alternatively, the MDC can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the MDC can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

To optimize transplant success, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the transplant procedure. For example, cyclosporin A or other immunosuppressive drugs can be administered to the transplant recipient. Immunological tolerance may also be induced prior to transplantation by alternative methods known in the art (D. J. Watt et al., 1984, *Clin. Exp. Immunol.* 55:419; D. Faustman et al., 1991, *Science* 252:1701).

Consistent with the present invention, the MDC can be administered to body tissues, including bone, epithelial tissue (i.e., skin, lumen, etc.), connective tissue (i.e., adipose, cartilage, ligament, lymph, etc.), muscle tissue (i.e., skeletal/striated or smooth muscle), and various organ tissues such as those organs that are associated with the digestive system (i.e., mouth, tongue, esophagus, stomach, liver, pancreas, gall bladder, intestine, anus, etc.), cardiovascular system (i.e., heart, veins, arteries, capillaries, etc.), respiratory system (i.e., lungs, trachea, etc.), reproductive system (i.e., vas deferens, scrotum, testes, penis, fallopian tubes, vagina, clitoris, uterus, breasts, ovaries, vulva, etc.), urological system (i.e., bladder, urethra, ureter, kidneys, etc.), and nervous system (i.e., brain, spinal cord, nerves, etc.).

The number of cells in an MDC suspension and the mode of administration may vary depending on the site and condition being treated. As non-limiting examples, in accordance with the present invention, about $1-1.5 \times 10^6$ MDC are injected for the treatment of an approximately 8 mm diameter region of cryodamage in bladder smooth muscle tissue (see Example 6), while about $0.5-1.0 \times 10^6$ MDC are administered via a collagen sponge matrix for the treatment of an approximately 5 mm region of skull defect (see Example 9). Consistent with the Examples disclosed herein, a skilled practitioner can modulate the amounts and methods of MDC-based treatments according to requirements, limitations, and/or optimizations determined for each case.

Dermatological conditions: The MDC and compositions thereof according to the present invention have marked utility as materials for soft tissue augmentation in cosmetic procedures, e.g., plastic surgery or anti-aging procedures. Specifically, such MDC and MDC-containing compositions can be used to treat various dermatological conditions in a human or animal subject, including, but not limited to, wounds, wrinkles, rhytids, cutaneous depressions of non-traumatic origin, stretch marks, depressed scars, scaring from acne vulgaris, and hypoplasia of the lip. More specifically, the MDC and compositions of the present invention can be used to treat wrinkles, rhytids, or cutaneous depressions of the face, and especially, the region surrounding the eye(s). To treat dermatological conditions, the MDC are prepared as disclosed herein and then administered, e.g. via injection, to the skin, subcutaneously or intradermally, to fill, bulk up, or repair the defect. The number of MDC introduced is modulated to repair deep cutaneous depressions or defects, as well as superficial surface depressions or defects, as required. For example, about $1-1.5 \times 10^6$ MDC are utilized for the augmentation of an approximately 5 mm region of the skin (see Example 3).

Conditions of the lumen: In another embodiment, the MDC and compositions thereof according to the present invention have further utility as treatments for conditions of the lumen in an animal or mammal subject, including humans. Specifically, the muscle-derived progenitor cells are used for completely or partially blocking, enhancing, enlarging, sealing, repairing, bulking, or filling various biological lumens or voids within the body. Lumens include, without limitation, blood vessels, intestine, stomach, esophagus, urethra, vagina, Fallopian tubes, vas deferens, and trachea. Voids may include, without limitation, various tissue wounds (i.e., loss of muscle and soft tissue bulk due to trauma; destruction of soft tissue due to penetrating projectiles such as a stab wound or bullet wound; loss of soft tissue from disease or tissue death due to surgical removal of the tissue including loss of breast tissue following a mastectomy for breast cancer or loss of muscle tissue following surgery to treat sarcoma, etc.), lesions, fissures, diverticulae, cysts, fistulae, aneurysms, and other undesirable or unwanted depressions or openings that may exist within the body of an animal or mammal, including humans. For the treatment of conditions of the lumen, the MDC are prepared as disclosed herein and then administered, e.g. via injection or intravenous delivery, to the lumenal tissue to fill or repair the void. The number of MDC introduced is modulated to repair large or small voids in a soft tissue environment, as required.

Conditions of the sphincter: The MDC and compositions thereof according to the present invention can also be used for the treatment of a sphincter injury, weakness, disease, or dysfunction in an animal or mammal, including humans. In particular, the MDC are used to augment tissues of the esophageal, anal, cardiac, pyloric, and urinary sphincters. More specifically, the present invention provides soft tissue augmentation treatments for gastroesophageal reflux symptoms, and urinary and fecal incontinence. For the treatment of sphincter defects, the MDC are prepared as described herein and then administered to the sphincter tissue, e.g. via injection, to provide additional bulk, filler, or support. The number of MDC introduced is modulated to provide varying amounts of bulking material as required. For example, about $1–1.5\times10^6$ MDC are used to provide augmentation for an approximately 5 mm region of the gastroesophageal junction or an approximately 5–10 mm region of the anal sphincter (see Example 4).

Muscle augmentation and contractility: In yet another embodiment of the present invention, the MDC and compositions thereof are used for the treatment of muscle conditions in a human or animal subject. In particular, the MDC can be used to augment the skeletal or smooth muscles to treat weakness or dysfunction caused by injury, disease, inactivity, or anoxia- or surgery-induced trauma. More specifically, the present invention provides treatments for skeletal muscle weakness or dysfunction, such as a sports-related injury. The present invention also provides treatments for smooth muscle disease or dysfunction, such as heart failure, or injury associated with myocardial infarction.

For muscle augmentation or treatment of muscle-related conditions, the MDC are prepared as described above and are administered, e.g. via injection, into muscle tissue to provide additional bulk, filler, or support. As is appreciated by the skilled practitioner, the number of MDC introduced is modulated to provide varying amounts of bulking material, as needed or required. For example, about $1–1.5\times10^6$ MDC are injected for the augmentation of an approximately 5 mm region of heart tissue (see Example 7).

In addition, the MDC and compositions thereof can be used to affect contractility in smooth muscle tissue, such as gastrointestinal tissue, esophageal tissue, and bladder tissue, as example. Indeed, muscle contractility was seen to be restored in cryodamaged bladder tissue after the introduction of muscle-derived progenitor cells, i.e., MDC, as demonstrated in Example 6. Thus, the present invention also embraces the use of MDC of the invention in restoring muscle contraction, and/or ameliorating or overcoming smooth muscle contractility problems, such decreased gastrointestinal motility, including the esophagus, stomach and intestine smooth muscle. A specific, yet nonlimiting example of a condition that the MDC of the invention can improve, reduce, or correct is gastroparesis, i.e., poor motility and emptying of the stomach.

Genetically Engineered Muscle-Derived Cells

In another aspect of the present invention, the MDC of this invention may be genetically engineered to contain a nucleic acid sequence(s) encoding one or more active biomolecules, and to express these biomolecules, including proteins, polypeptides, peptides, hormones, metabolites, drugs, enzymes, and the like. Such MDC may be histocompatible (autologous) or nonhistocompatible (allogeneic) to the recipient, including humans. These cells can serve as long-term local delivery systems for a variety of treatments, for example, for the treatment of such diseases and pathologies as cancer, transplant rejection, and the regeneration of muscle and nerve tissues, diabetes, liver failure, renal failure, neural defects and diseases such as Parkinson's disease, and to deliver a gene product to a site of tissue augmentation, or void filling, such as a therapeutic agent, as described herein.

Preferred in the present invention are autologous muscle-derived progenitor cells, which will not be recognized as foreign to the recipient. In this regard, the MDC used for cell-mediated gene transfer or delivery will desirably be matched vis-à-vis the major histocompatibility locus (MHC or HLA in humans). Such MHC or HLA matched cells may be autologous. Alternatively, the cells may be from a person having the same or a similar MHC or HLA antigen profile. The patient may also be tolerized to the allogeneic MHC antigens. The present invention also encompasses the use of cells lacking MHC Class I and/or II antigens, such as described in U.S. Pat. No. 5,538,722.

The MDC may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. MDC can be transfected or transduced by different vectors and thus can serve as gene delivery vehicles to transfer the expressed products into muscle.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, and the like.

Vectors for introducing heterologous (i.e., foreign) nucleic acid (DNA or RNA) into muscle cells for the expression of bioactive products are well known in the art. Such vectors possess a promoter sequence, preferably, a promoter that is cell-specific and placed upstream of the sequence to be expressed. The vectors may also contain, optionally, one or more expressible marker genes for expression as an indication of successful transfection and expression of the nucleic acid sequences contained in the vector.

Illustrative examples of vehicles or vector constructs for transfection or infection of the muscle-derived cells of the present invention include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. Examples of such functional sequences include polynucleotide, e.g., DNA or RNA, sequences comprising transcriptional and translational initiation and termination regulatory sequences, including promoters (e.g., strong promoters, inducible promoters, and the like) and enhancers which are active in muscle cells.

Also included as part of the functional sequences is an open reading frame (polynucleotide sequence) encoding a protein of interest; flanking sequences may also be included for site-directed integration. In some situations, the 5'-flanking sequence will allow homologous recombination, thus changing the nature of the transcriptional initiation region, so as to provide for inducible or noninducible transcription to increase or decrease the level of transcription, as an example.

In general, the nucleic acid sequence desired to be expressed by the muscle-derived progenitor cell is that of a structural gene, or a functional fragment, segment or portion of the gene, that is heterologous to the muscle-derived progenitor cell and encodes a desired protein or polypeptide product, for example. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, cell differentiation factors, cell signaling factors and programmed cell death factors. Specific examples include, but are not limited to, genes encoding BMP-2 (rhBMP-2), IL-1Ra, Factor IX, and connexin 43.

As mentioned above, a marker may be present for selection of cells containing the vector construct. The marker may be an inducible or non-inducible gene and will generally allow for positive selection under induction, or without induction, respectively. Examples of commonly-used marker genes include neomycin, dihydrofolate reductase, glutamine synthetase, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the muscle-derived cells. Such replication systems are represented by replication-defective adenovirus constructed as described, for example, by G. Acsadi et al., 1994, *Hum. Mol. Genet* 3:579–584, and by Epstein-Barr virus. Examples of replication defective vectors, particularly, retroviral vectors that are replication defective, are BAG, described by Price et al., 1987, *Proc. Natl. Acad. Sci. USA,* 84:156; and Sanes et al., 1986, *EMBO J.,* 5:3133. It will be understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

If desired, infectious replication-defective viral vectors may be used to genetically engineer the cells prior to in vivo injection of the cells. In this regard, the vectors may be introduced into retroviral producer cells for amphotrophic packaging. The natural expansion of muscle-derived progenitor cells into adjacent regions obviates a large number of injections into or at the site(s) of interest.

In another aspect, the present invention provides ex vivo gene delivery to cells and tissues of a recipient mammalian host, including humans, through the use of MDC, e.g., early progenitor muscle cells, that have been virally transduced using an adenoviral vector engineered to contain a heterologous gene encoding a desired gene product. Such an ex vivo approach provides the advantage of efficient viral gene transfer, which is superior to direct gene transfer approaches. The ex vivo procedure involves the use of the muscle-derived progenitor cells from isolated cells of muscle tissue. The muscle biopsy that will serve as the source of muscle-derived progenitor cells can be obtained from an injury site or from another area that may be more easily obtainable from the clinical surgeon.

It will be appreciated that in accordance with the present invention, clonal isolates can be derived from the population of muscle-derived progenitor cells (i.e., PP6 cells) using various procedures known in the art, for example, limiting dilution plating in tissue culture medium. Clonal isolates comprise genetically identical cells that originate from a single, solitary cell. In addition, clonal isolates can be derived using FACS analysis as described above, followed by limiting dilution to achieve a single cell per well to establish a clonally isolated cell line. An example of a clonal isolate derived from the PP6 cell population is mc13, which is described in Example 9. Preferably, MDC clonal isolates are utilized in the present methods, as well as for genetic engineering for the expression of one or more bioactive molecules, or in gene replacement therapies.

The MDC are first infected with engineered viral vectors containing at least one heterologous gene encoding a desired gene product, suspended in a physiologically acceptable carrier or excipient, such as saline or phosphate buffered saline, and then administered to an appropriate site in the host. Consistent with the present invention, the MDC can be administered to body tissues, including bone, epithelial tissue, connective tissue, muscle tissue, and various organ tissues such as those organs that are associated with the digestive system, cardiovascular system, respiratory system, reproductive system, urological system, and nervous system, as described above. The desired gene product is expressed by the injected cells, which thus introduce the gene product into the host. The introduced and expressed gene products can thereby be utilized to treat, repair, or ameliorate the injury, dysfunction, or disease, due to their being expressed over long time periods by the MDC of the invention, having long-term survival in the host.

In animal model studies of myoblast-mediated gene therapy, implantation of $10^6$ myoblasts per 100 mg muscle was required for partial correction of muscle enzyme defects (see, J. E. Morgan et al., 1988, *J. Neural. Sci.* 86:137; T. A. Partridge et al., 1989, *Nature* 337:176). Extrapolating from this data, approximately $10^{12}$ MDC suspended in a physiologically compatible medium can be implanted into muscle tissue for gene therapy for a 70 kg human. This number of MDC of the invention can be produced from a single 100 mg skeletal muscle biopsy from a human source (see below). For the treatment of a specific injury site, an injection of genetically engineered MDC into a given tissue or site of injury comprises a therapeutically effective amount of cells in solution or suspension, preferably, about $10^5$ to $10^6$ cells per $cm^3$ of tissue to be treated, in a physiologically acceptable medium.

EXAMPLES

Example 1

MDC Enrichment, Isolation and Analysis

Enrichment and isolation of MDC: MDC were prepared as described (U.S. Pat. No. 6,866,842 of Chancellor et al.). Muscle explants were obtained from the hind limbs of a number of sources, namely from 3-week-old mdx (dystrophic) mice (C57BL/10ScSn mdx/mdx, Jackson Laboratories), 4–6 week-old normal female SD (Sprague Dawley) rats, or SCID (severe combined immunodeficiency) mice. The muscle tissue from each of the animal sources was dissected to remove any bones and minced into a slurry. The slurry was then digested by 1 hour serial incubations with 0.2% type XI collagenase, dispase (grade II, 240 unit), and 0.1% trypsin at 37° C. The resulting cell suspension was passed through 18, 20, and 22 gauge needles and centrifuged at 3000 rpm for 5 minutes. Subsequently, cells were suspended in growth medium (DMEM supplemented with 10% fetal bovine serum, 10% horse serum, 0.5% chick embryo extract, and 2% penicillin/streptomycin). Cells were then preplated in collagen-coated flasks (U.S. Pat. No. 6,866,842 of Chancellor et al.). After approximately 1 hour, the supernatant was removed from the flask and re-plated into a fresh collagen-coated flask. The cells which adhered rapidly within this 1 hour incubation were mostly fibroblasts (Z. Qu et al., supra; U.S. Pat. No. 6,866,842 of Chancellor et al.). The supernatant was removed and re-plated after 30–40% of the cells had adhered to each flask. After approximately 5–6 serial platings, the culture was enriched with small, round cells, designated as PP6 cells, which were isolated from the starting cell population and used in further studies. The adherent cells isolated in the early platings were pooled together and designated as PP1–4 cells.

The mdx PP1–4, mdx PP6, normal PP6, and fibroblast cell populations were examined by immunohistochemical analysis for the expression of cell markers. The results of this analysis are shown in Table 1.

TABLE 1

Cell markers expressed in PP1–4 and PP6 cell populations.

| | mdx PP1–4 cells | mdx PP6 cells | nor PP6 cells | fibroblasts |
|---|---|---|---|---|
| desmin | +/− | + | + | − |
| CD34 | − | + | + | − |
| Bcl-2 | (−) | + | + | − |
| Flk-1 | na | + | + | − |
| Sca-1 | na | + | + | − |
| M-cadherin | −/+ | −/+ | −/+ | − |
| MyoD | −/+ | +/− | +/− | − |
| myogenin | −/+ | +/− | +/− | − |

Mdx PP1–4, mdx PP6, normal PP6, and fibroblast cells were derived by preplating technique and examined by immunohistochemical analysis. "−" indicates less than 2% of the cells showed expression; "(−)"; "−/+" indicates 5–50% of the cells showed expression; "+/−" indicates ~40–80% of the cells showed expession; "+" indicates that >95% of the cells showed expression; "nor" indicates normal cells; "na" indicates that the immunohistochemical data is not available.

It is noted that both mdx and normal mice showed identical distribution of all of the cell markers tested in this assay. Thus, the presence of the mdx mutation does not affect the cell marker expression of the isolated PP6 muscle-cell derived population.

MDC were grown in proliferation medium containing DMEM (Dulbecco's Modified Eagle Medium) with 10% FBS (fetal bovine serum), 10% HS (horse serum), 0.5% chick embryo extract, and 1% penicillin/streptomycin, or fusion medium containing DMEM supplemented with 2% fetal bovine serum and 1% antibiotic solution. All media supplies were purchased through Gibco Laboratories (Grand Island, N.Y.).

Example 2

MDC Vectors and Transfection

Retrovirus and adenovirus vectors: The MFG-NB (N. Ferry et al., 1991, *Proc. Natl. Acad. Sci. USA* 88:8377–81) retroviral vector was used for the MDC experiments. This vector contains a modified LacZ gene (NLS-LacZ) that includes a nuclear-localization sequence cloned from the simian virus (SV40) large T antigen transcribed from the long terminal repeat (LTR). The retroviral stock was grown and prepared as previously described (J. C. van Deutekom et al., 1998, *Neuromuscul. Disord.* 8:135–48). The retrovirus was titered to $1\times10^7$–$1\times10^9$ cfu/ml.

An adenovirus vector was also used. This vector contained the LacZ gene under the control of the human cytomegalovirus (HuCMV) promoter (J. Huard et al., 1994, *Hum Gene Ther* 5:949–58). The E1–E3 deleted recombinant adenovirus was obtained through Dr. I. Kovesdi (Gene Vec Inc., Rockville, Md.).

Viral transduction of MDC: For viral transduction, MDC were plated at a density of $1$–$1.5\times10^6$ in T 75 flasks. PP6 MDC were washed in HBSS (Hank's Balanced Salt Solution) and incubated with either retrovirus ($1\times10^7$–$1\times10^9$ cfu/ml) or adenovirus ($1\times10^9$ cfu/ml) suspensions in 5 ml of DMEM containing 8 μg/ml Polybrene™ (Abbott Laboratories, Chicago, Ill.) for 4 h at 37° C. Virally transduced MDC were grown in 10 ml of proliferation medium for 24 h at 37° C. MDC were then rinsed with HBSS and enzymatically digested with 0.25% trypsin for 1 minute. The treated, virally transduced MDC were centrifuged for 5 minutes at 3,500 rpm, and the pellet was resuspended in 20 μl of HBSS.

Example 3

Soft Tissue Augmentation of the Skin

MDC and collagen injection: SD rats were prepared for surgery by anesthetizing with halothane using standard methods, and washing the surgical site with Betadine® solution. The skin of the lower abdomen was injected with either 10 microliters (μl) of a MDC suspension in HBSS (approximately $1$–$1.5\times10^6$ cells), 10 μl of commercially available bovine collagen (Contigen™; C. R. Bard, Covington, Ga.), or 10 μl of sterile saline using a Hamilton microsyringe. At 5 days, 2 weeks and 4 weeks post-injection, the area surrounding each injection site was excised, prepared for histochemical analysis, examined microscopically, and photographed. Histochemical analysis included hematoxylin, eosin, or trichrome staining.

Figure 1B:
Figure 1C:
Figure 1D:
Figure 1E:
Figure 1F:

The results demonstrate that MDC were viable for up to at least 4 weeks following injection into skin tissue, with no evidence of inflammation of the tissue at the injection site (FIGS. 1D–1F). In contrast, collagen was not visible at 2 weeks following injection into skin tissue (FIGS. 1B and 1C). Thus, MDC compositions can be used as skin augmentation materials for use, for example, in cosmetic and aesthetic applications or surgery. This is an unexpected finding, since it was previously believed that transplanted muscle cells needed surrounding host muscle fibers with which to attach in order to survive. The survival of the MDC of the present invention following injection into non-muscle tissue is further demonstrated in Examples 8 and 9.

Example 4

Soft Tissue Augmentation of the Gastroesophageal Junction and Anal Sphincter

Figure 2B:
FIGS. 2A and 2B illustrate the results of lower esophageal (FIG. 2A) and anal sphincter (FIG. 2B) soft tissue augmentation utilizing injections of MDC compositions. Injections were made into the gastroesophageal junction or anal sphincter. At day 3 post-injection, tissue samples were obtained and prepared for analysis. MDC are indicated by β-galactosidase staining.
Figure 2A:
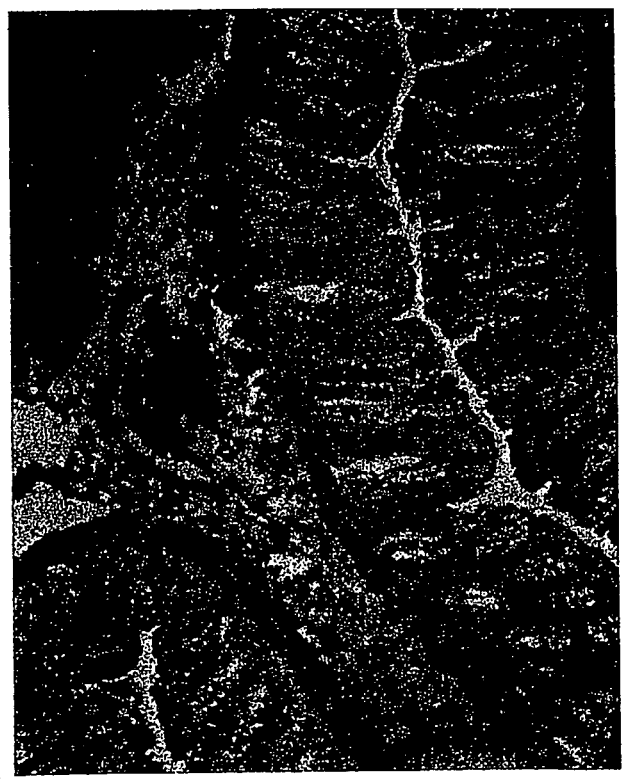

SD rats were prepared for surgery as described above. A midline abdomen incision was made to expose the gastroesophageal junction and anal sphincter. The soft tissue was injected with 10 μl of a suspension of muscle-derived progenitor cells of in HBSS (1–1.5×10⁶ cells) using a Hamilton microsyringe. At day 3 post-injection, the area surrounding each injection site was excised, prepared for histochemical analysis, stained for β-galactosidase to determine the location and viability of the cells carrying the LacZ marker, examined microscopically, and photographed. Results of these experiments demonstrate that MDC compositions can be used as esophageal and anal sphincter bulking materials (FIGS. 2A and 2B) for the treatment of gastroesophageal reflux or fecal incontinence symptoms or conditions.

Example 5

Soft Tissue Augmentation of Vesico-Ureteral Junction

Figure 3A:
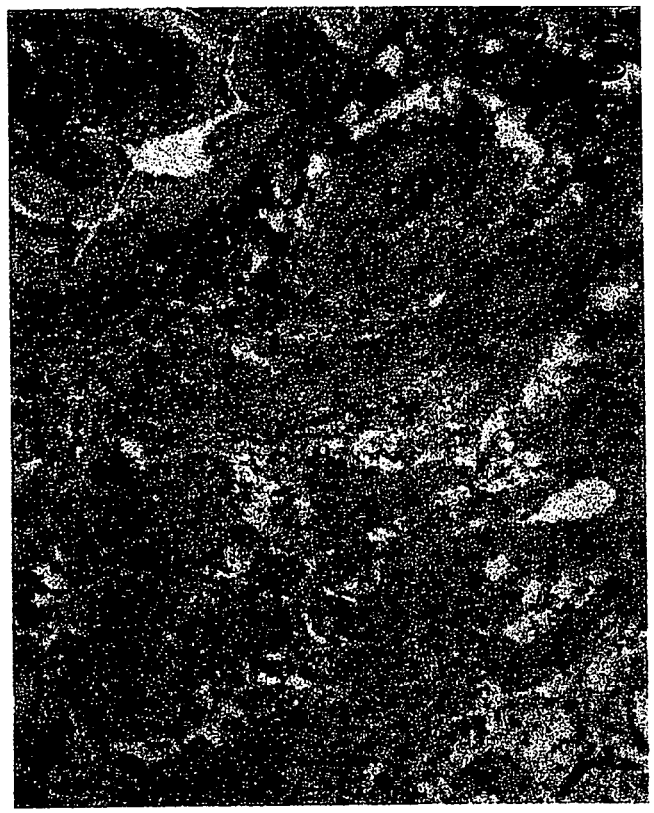
FIGS. 3A and 3B illustrate the results of bladder-ureteral junction soft tissue augmentation utilizing injections of MDC compositions. Injections were made into the vesicoureteral junction. At day 3 post-injection, tissue samples were obtained and prepared for analysis. MDC are indicated by β-galactosidase staining as viewed near the arrow.
Figure 3B:
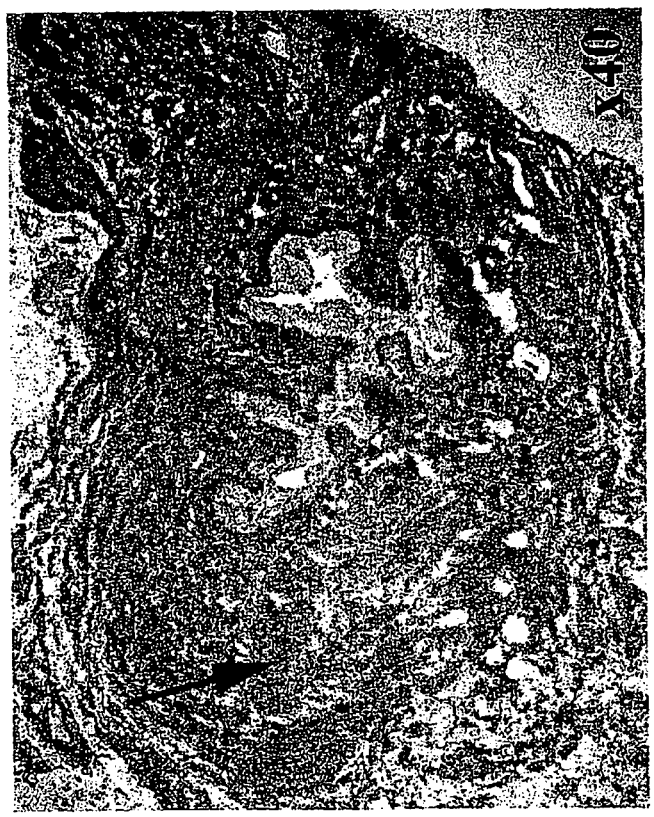
Figures 4A, 4B:
FIGS. 4A and 4B illustrate the treatment of bladder cryoinjury utilizing soft tissue injections of MDC compositions. Injections were made into the bladder wall at the site of cryoinjury. At day 30 post-injection, tissue samples were obtained and prepared for staining. Arrows indicate site of cryoinjury and MDC injection. Magnification is 100×.

SD rats were prepared for surgery as described above. A midline abdomen incision was made to expose the ureteral-bladder (vesico-ureteral) junction. The tissue was injected with 10 µl of MDC suspension in HBSS (1–1.5×10⁶ cells) using a Hamilton microsyringe. At 3 days post-injection, the area surrounding each injection site was excised, prepared for histological analysis, stained for β-galactosidase to determine the location and viability of the cells carrying the LacZ marker, examined microscopically, and photographed. These results demonstrate that MDC-based compositions can be used as utereral-bladder augmentation materials (FIGS. 3A and 3B) for the treatment of vesico-ureteral reflux symptoms or conditions.

Example 6

MDC Treatment of Cryodamaged Bladder Tissue

Cryoinjury and MDC transplantation: SD rats were prepared for surgery as described above. A low midline incision was made to expose the bladder and urethra. The bladder was then filled with 1 ml saline. Cryodamage was performed with an 8 mm diameter aluminum rod chilled on dry ice. The chilled probe was placed against one side of the bladder wall for 15 or 30 seconds (referred to as "mild" or "severe" damage, respectively). Immediately following cryoinjury, one severe damage group was injected with muscle-derived cells of the invention (1–1.5×10⁶ of cells in 15 µl HBSS), while a control severe damage group was injected with HBSS (15 µl) (n=3 per group). One week following cryoinjury, the other mild and severe damage groups were injected with an MDC suspension in 50 µl HBSS (2–3×10⁶ cells), while control mild and severe damage groups were injected with 50 µl HBSS (n=4 per group). For each group, injections were made into the center of the injured region using a 30-gauge needle and a Hamilton microsyringe.

Immunohistochemical staining for smooth muscle actin (α-SM actin): To prepare samples for immunohistochemical analysis, tissues or cell samples were fixed in cold acetone at −20° C. for 2 minutes, and blocked with 5% HS for 1 hour. The samples were incubated overnight at room temperature in a humidity chamber with mouse monoclonal anti-smooth muscle actin primary antibodies (Cat. # F-3777; Sigma Chemical Co., St. Louis, Mo.) (1:400 dilution in PBS pH 7.4). The samples were then washed 3 times with PBS, and incubated with anti-mouse IgG secondary antibodies conjugated with the Cy3 fluorochrome (Sigma Chemical Co.) (1:200 dilution in PBS pH 7.4).

Immunohistochemical staining for fast myosin heavy chain (Fast MyHC): Tissues or cell samples were fixed in cold acetone at −20° C. for 2 minutes and blocked with 5% HS for 1 hour. The samples were then incubated overnight at room temperature in a humidity chamber with mouse monoclonal anti-skeletal myosin (fast) primary antibodies (Cat. # M4276; Sigma Chemical Co.) (1:400 dilution in PBS pH 7.4). The samples were then washed 3 times with PBS, and incubated with Cy3 conjugated anti-mouse IgG secondary antibodies (Sigma Chemical Co.) (1:200 dilution in PBS pH 7.4).

Cell culture: Muscle derived progenitor cells as prepared in Example 1 were plated in 35 mm collagen-coated dishes in proliferation medium. After 24 hours, the proliferation medium was replaced with fusion medium. The cells were maintained in fusion medium with daily medium changes until the MDC differentiated into myotubes.

Contractility studies: Two weeks after the MDC injection, the animals were euthanized and used to prepare bladder strips. Two strips were prepared from each bladder, and both strips were cut to extend along the circumference of the bladder. The bladder strips were mounted in a tissue bath and subjected to neural contractions (20 Hz, 10 and 80 shocks), which were recorded and analyzed as described below.

Tissue harvest and histology: SD rats were euthanized and samples of the tissue surrounding the injection site were removed. The samples were flash frozen using 2-methylbutane pre-cooled in liquid nitrogen. Histochemical analysis of the samples included hematoxylin and eosin staining. The samples were stained, examined microscopically, and photographed. Each cryostat section measured 10 µm in thickness.

Electrostimulation of bladder smooth muscle tissue: The animal was euthanized and the bladder was quickly removed. Two strips covering the circumference of the bladder wall were obtained from each bladder. The strips were mounted in 5 ml organ baths containing Kreb's solution (113 mmol/l NaCl, 4.7 mmol/l KCl, 1.25 mmol/l $CaCl_2$, 1.2 mmol/l $MgSO_4$, 25 mmol/l $NaHCO_3$, 1.2 mmol/l $KH_2PO_4$, and 11.5 mmol/l glucose) aerated with 95% $O_2$ and 5% $CO_2$. The initial tension was set to 10 mN, and isometric contractions were measured with strain-gauge transducers coupled with a TBM4 strain gauge amplifier (World Precision Instruments). Contraction measurements were compiled using a data acquisition program (Windaq, DATAQ Instruments, Inc., Akron, Ohio). The sampling rate per channel was set to 100 Hz. The amplitude of the contractions was computed using a calculation program (WindaqEx, DATAQ Instruments, Inc.). Following a 20 minutes equilibration period, electrical field stimuli were applied through two platinum wire electrodes separated by 4 cm at the top and the bottom of the organ bath. The temperature was maintained at 37° C. throughout the experiment.

Chemical stimulation of bladder smooth muscle tissue: The bladder strips were stimulated with square wave pulses of 0.25 msec duration with maximal voltage (100 V) and a frequency response curve constructed using 10 or 80 shocks at 1, 2, 5, 10, 20, or 40 Hz. Following electrostimulation, 5, 10, or 20 µM carbachol was added to the bladder strips to induce contractions. In parallel experiments, 1 µM atropine was added, electrostimulation was applied as above, and 50 µM methylene ATP was added to induce contractions.

Staining for innervation: Acetylcholine (Ach) staining was used to assess the reinnervation of MDC in smooth muscle. Ach is a stain for the neuromuscular junction that indicates the presence of nerve endings. Following MDC injection, tissue was excised at day 3, 15, 30, or after 6 months, stained for Ach, observed by microscopy, and photographed.

Statistical analysis: Values are reported as means±standard deviations. A "P" value of less than 0.05 was considered statistically significant. Student's test was used.

Figures 5G, 5H, 5I:

MDC differentiation: Muscle derived progenitor cells as prepared in Example 1 were evaluated for cellular differentiation. Alpha-SM actin is the earliest known marker for the smooth muscle cell phenotype (K. M. McHugh, 1995, *Dev. Dyn.* 204:278–90), and the main marker of the myofibroblastic phenotype (I. Darby et al., 1990, *Lab. Invest.* 63:21–9). During muscle cell differentiation, expression of α-SM actin decreases, while fast MyHC expression increases. Histochemical analysis of MDC-treated bladder tissues utilizing α-SM actin and fast MyHC markers demonstrates the differentiation of MDC following injection into site of cryoinjury. At day 5 following injection into cryodamaged bladder tissue, several MDC (at least 20%) show α-SM actin staining (FIG. 5B), indicating that the cells are still undifferentiated. After 6 months following injection, however, virtually all MDC have differentiated into myotubes or myofibers, as shown by an decrease in α-SM actin staining (FIG. 5F), with a concomitant increase in fast MyHC staining (FIG. 5I).

Figure 6A:
FIGS. 6A–6D illustrate the reinnervation of MDC injected into the soft tissue of the urinary bladder. Innervation is indicated by acetylcholine (Ach) staining, which shows the neuromuscular junction. At day 3 post-injection, few innervations are observed, as shown by Ach staining (FIG. 6A). At day 15 post injection, several innervations are observed (FIG. 6B). At day 30 post-injection, more innervations are observed (FIG. 6C). After 6 months post-injection, numerous innervations are observed at low (100×) magnification (FIG. 6D).
Figure 6B:
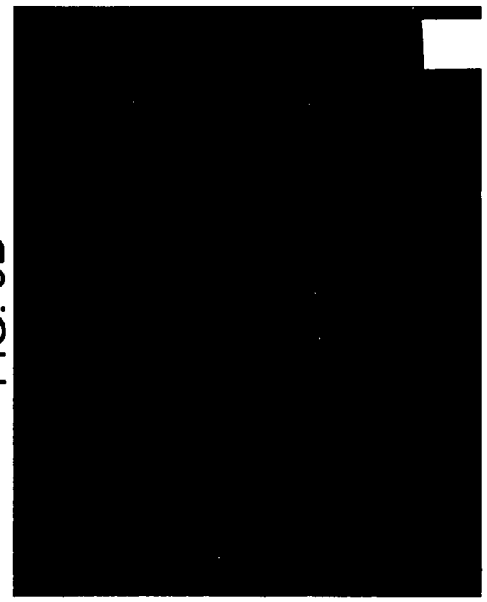
Figure 6C:
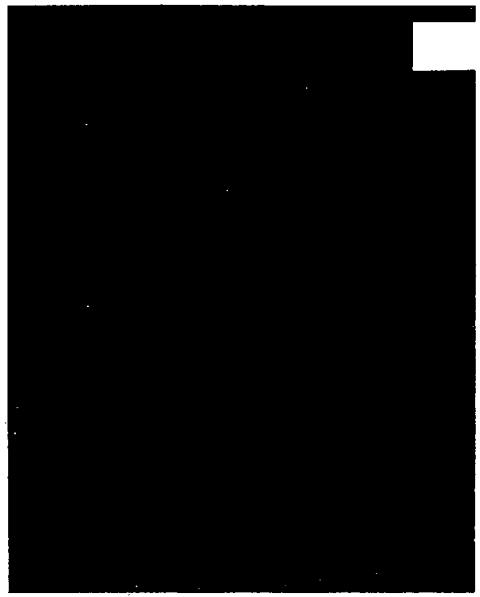
Figure 6D:
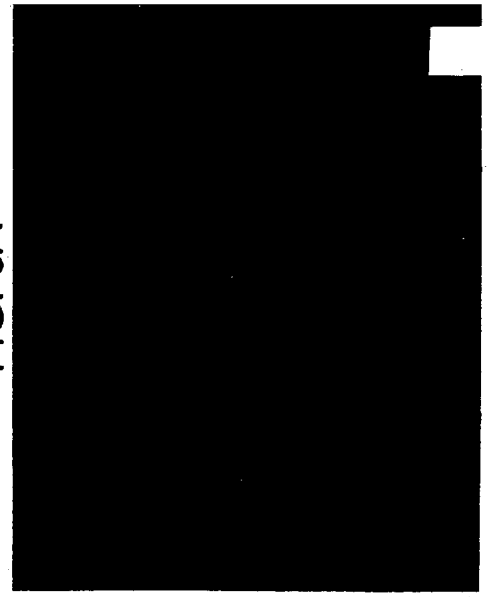

Muscle reinnervation: Because acetylcholine (Ach) is present at the neuromuscular junction, it can serve as an indicator of muscle innervation. Histochemical analysis of MDC-treated bladder tissues utilizing the Ach marker demonstrates the reinnervation of the MDC following injection into sites of cryodamage. At day 3 following injection into cryodamaged bladder tissue the injected MDC show minimal innervation, as indicated by relatively low levels of Ach staining (FIG. 6A). At day 15 post-injection, increased levels of innervation are observed, as indicated by increased levels of Ach staining (FIG. 6B). At day 30 post-injection, still more Ach staining is observed (FIG. 6C), indicative of further increases in innervation. At 6 months following injection, extensive innervation is observed, as indicated by substantial Ach staining throughout the MDC injected area viewed at low magnification (FIG. 6D). These results indicate that the pelvic nerve is growing into the MDC injected area of the bladder, and suggest that the MDC can improve the contractility and function of the injected tissue.

Contractility Physiology studies: To determine whether injected MDC improved the function of the treated bladder tissues, several contractility studies were completed (see above). Table 2 presents the data showing the contractile parameters of bladder muscle following cryoinjury with or without MDC injections.

TABLE 2

Contractile parameters of bladder muscle following cryoinjury.

| Group No. | | Contraction amplitude (mN/mg) | | Velocity (contraction) (mN/s) | | No. of specimens |
|---|---|---|---|---|---|---|
| | | 20 Hz/10 shocks | 20 Hz/80 shocks | 20 Hz/10 shocks | 20 Hz/80 shocks | |
| 1 | Sham | 0.375 ± 0.24 | 0.697 ± 0.46 | 18.08 ± 8.15 | 15.56 ± 8.39 | 6 |
| | MDC | 0.368 ± 0.26 | 0.812 ± 0.31 | 16.23 ± 10.3 | 16.38 ± 7.54 | 6 |
| 2 | Sham | 0.427 ± 0.17 | 0.966 ± 0.31 | 22.96 ± 8.93 | 24.56 ± 5.03 | 8 |
| | MDC | 0.539 ± 0.24 | 1.161 ± 0.55 | 27.86 ± 14.08 | 30.59 ± 13.05 | 8 |
| 3 | Sham | 0.389 ± 0.14* | 0.708 ± 0.26** | 25.70 ± 5.87 | 24.24 ± 6.38 | 8 |
| | MDC | 0.564 ± 0.16* | 1.139 ± 0.29** | 30.59 ± 17.8 | 29.31 ± 15.3 | 8 |
| 4 | Normal | 0.927 ± 0.23 | 1.748 ± 0.52 | 34.23 ± 8.82 | 29.05 ± 7.06 | 6 |

*$p < 0.05$,
**$p < 0.01$

Values are means ± standard deviations. For statistical analysis, Student's test was performed for control and MDC injection groups. Group No. 1: severe damage group with immediate MDC injections following cryoinjury. Group No. 2: mild damage group with MDC injections one week following cryodamage. Group No. 3: severe damage group with MDC injections one week following cryodamage. Group No. 4: normal bladder tissue.

The severe damage group injected with MDC immediately following cryoinjury (Group 1) showed similar contractility as the control (sham) group (compare contractility levels shown in sham and MDC rows in Group 1, Table 2). However, the severe damage group injected with MDC one week following the cryodamage (Group 3) showed increased contraction amplitude (145% and 161% of the control bladder at 20 Hz/10 shocks and 20 Hz/80 shocks, respectively) compared with the control group (compare contractile amplitude levels shown in sham and MDC rows indicated with asterisks in Table 2). Similarly, the severe damage group injected with MDC one week following the cryodamage (Group 3) showed increased contraction velocity (119% and 121% of that of the control strip at 20 Hz/10 shocks and 20 Hz/80 shocks, respectively) compared with the control group (compare contractile velocity values in sham and MDC rows in Group 3, Table 2). The mild damage group injected with MDC one week following the cryodamage (Group 2) also showed increased contraction amplitude and velocity compared to the control group (compare contractility levels shown in sham and MDC rows in Group 2, Table 2). The results of these studies show that MDC injections can restore contractility to cryodamaged bladder muscle tissue, and indicate that MDC-based compositions can be utilized for the treatment of urinary incontinence.

Example 7

Soft Tissue Augmentation of the Myocardium

Figure 7A:
FIGS. 7A and 7B illustrate the results of soft tissue augmentation of myocardial smooth muscle utilizing injections of MDC compositions. Injections were made into the ventricular wall, and tissue samples were prepared 3 days post-injection. MDC are indicated by β-galactosidase staining.
Figure 7B:
Figure 8A:
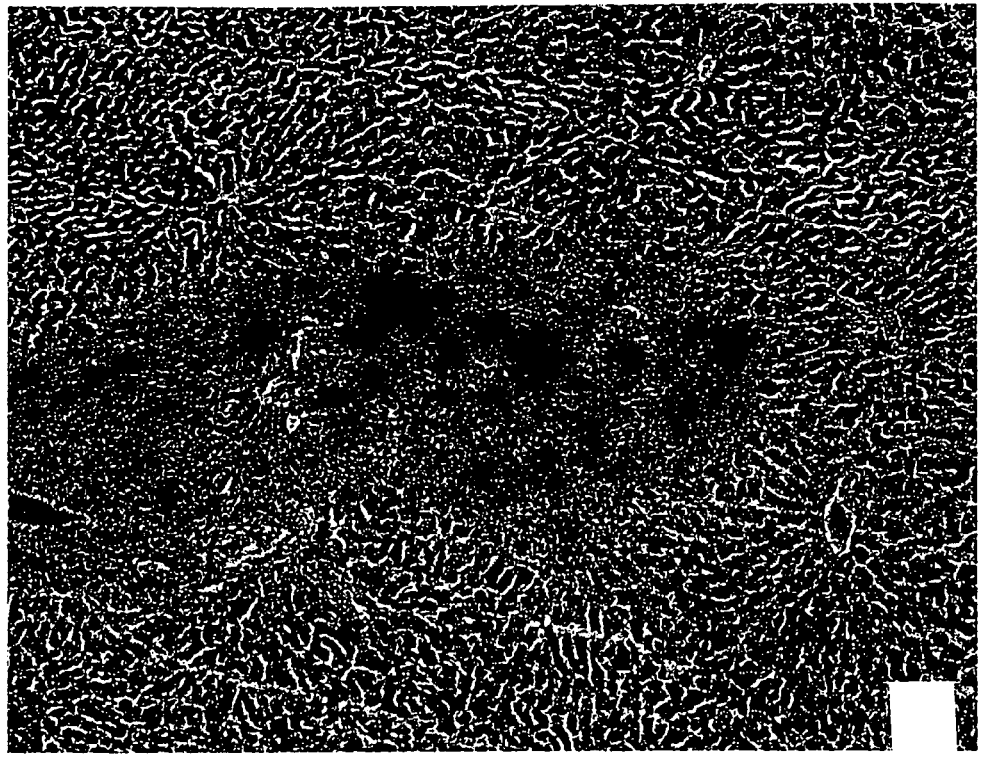
FIGS. 8A and 8B illustrate the results of MDC injections into liver tissue. Injections were made into liver tissue in the lower left lobe, and tissue samples were prepared 4 days post-injection. MDC are indicated by β-galactosidase staining.
Figure 8B:
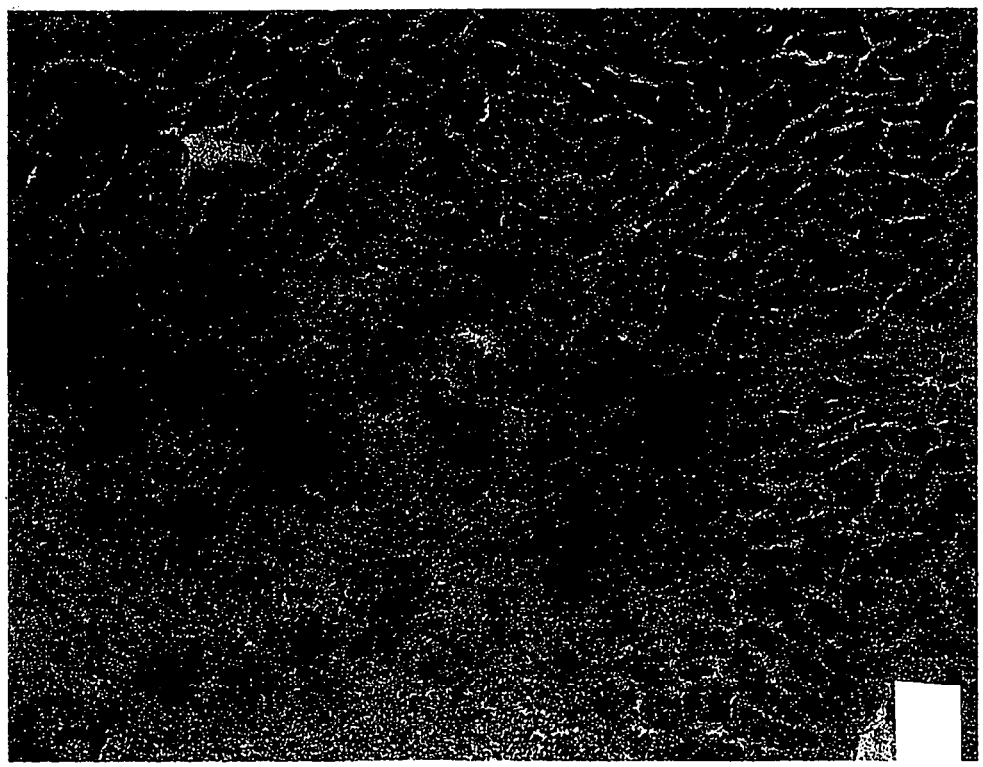
Figure 9A:
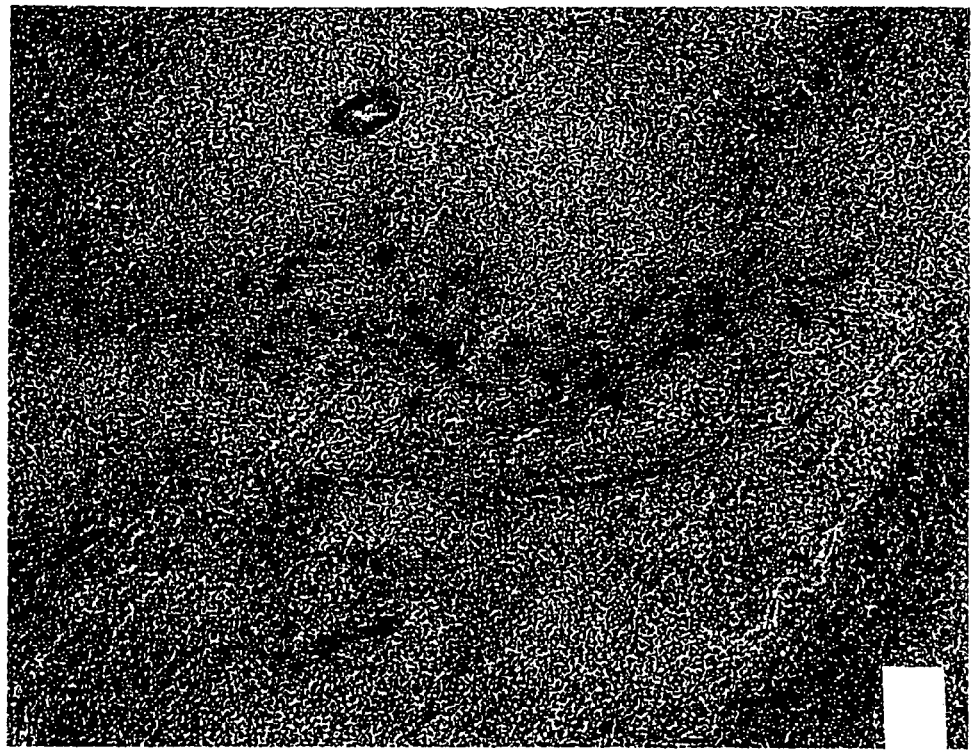
FIGS. 9A and 9B illustrate the results of MDC injections into spleen tissue. Injections were made into spleen tissue in the interior aspect, and tissue samples were prepared 4 days post-injection. MDC are indicated by β-galactosidase staining.
Figure 9B:
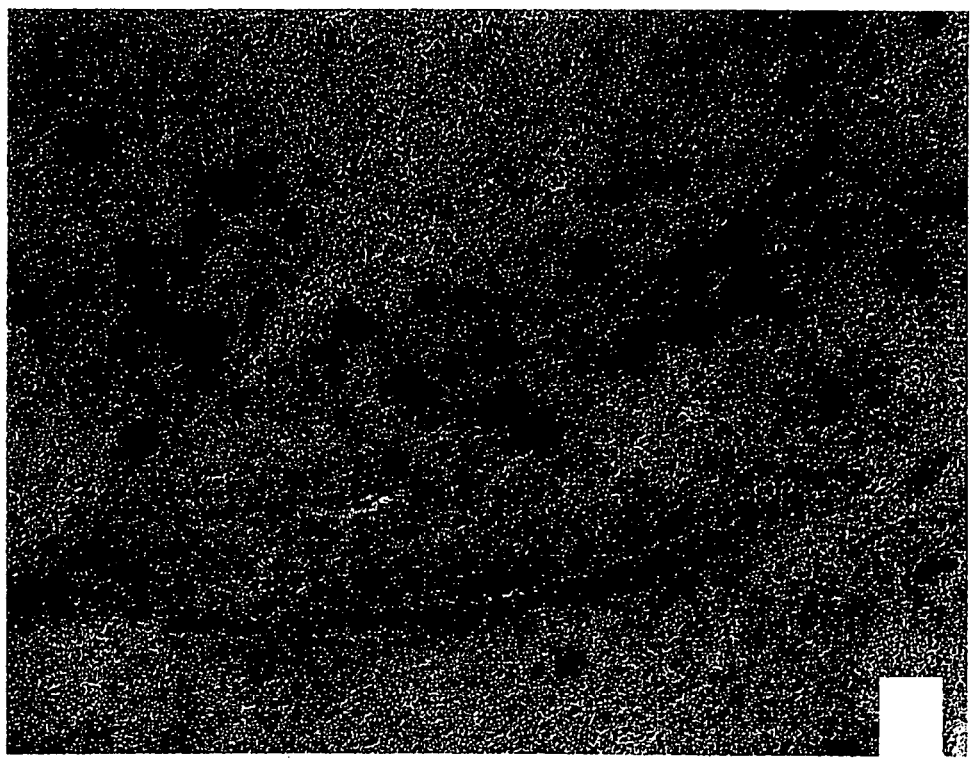
Figure 10A:
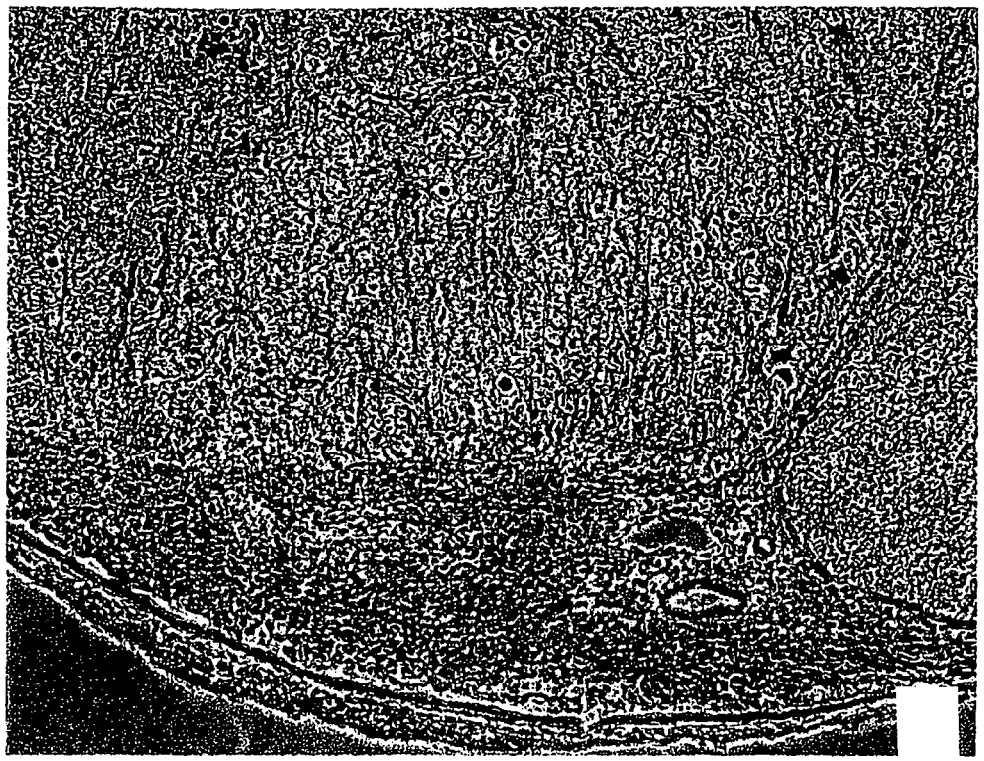
FIGS. 10A and 10B illustrate the results of MDC injections into spinal cord tissue. Injections were made into spinal cord tissue, and tissue samples were prepared 4 days post-injection. MDC are indicated by β-galactosidase staining.
Figure 10B:
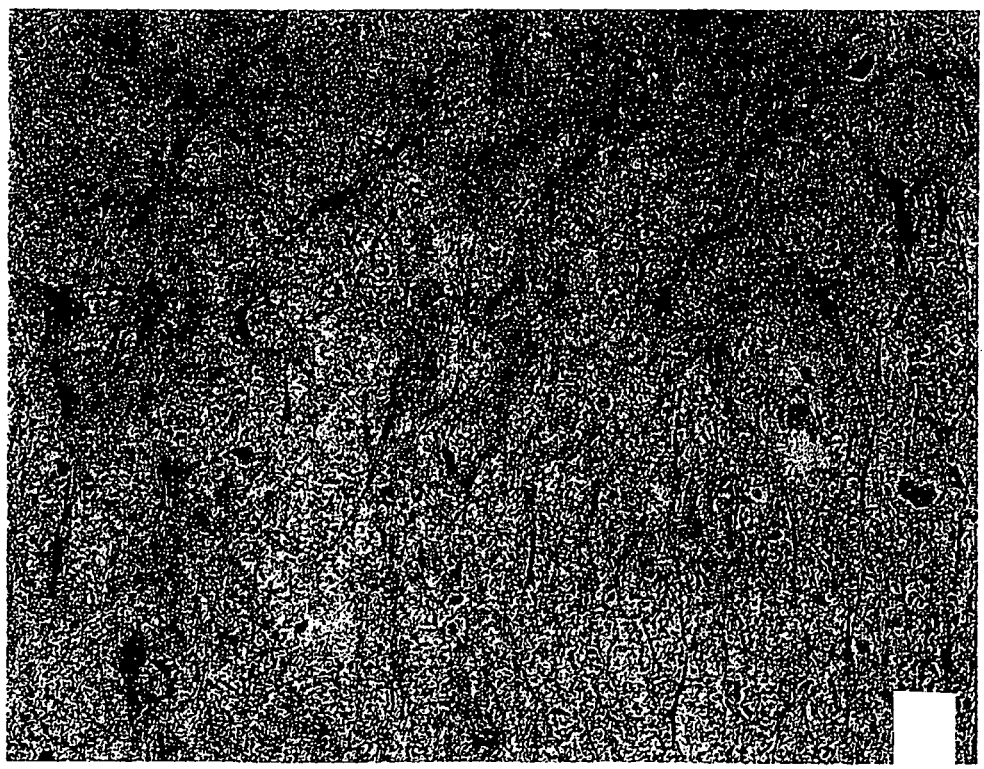
Figure 11A:
Figure 11G:
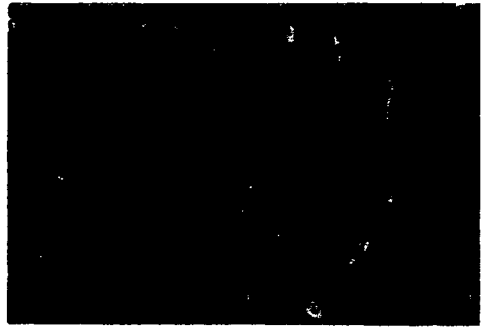
Figure 11B:
Figure 11H:
Figure 11C:
Figure 11I:

SD rats were prepared for surgery as described above. A thoracic incision was made to expose the heart. The ventricular wall was injected with 10 μl of MDC suspension in HBSS ($1–1.5×10^6$ cells) using a Hamilton microsyringe. At day 3, the area surrounding each injection site was excised, prepared for histochemical analysis, stained for β-galactosidase to determine the location and viability of the cells carrying the LacZ marker, examined microscopically, and photographed. The results of these experiments demonstrate that MDC compositions can be used as myocardial soft tissue augmentation materials (FIGS. 7A and 7B) for the treatment of injury or weakness secondary to heart failure or myocardial infarction.

Example 8

MDC Injection into Liver, Spleen, and Spinal Cord Tissues

SD rats were prepared for surgery as described above. A midline abdomen incision was made to expose the liver and spleen. Both sites were injected with 10 µl of MDC suspension in HBSS ($1$–$1.5 \times 10^6$ cells) using a Hamilton microsyringe. At the same time, a midline back incision and a partial laminectomy was made to expose the spinal cord. Spinal cord tissues at level T10 were then injected with the MDC suspension in HBSS as done for the liver and spleen tissues. At day 4, the area surrounding each injection site was excised, prepared histochemical analysis, stained for β-galactosidase to determine the location and viability of the cells carrying the LacZ marker, examined microscopically, and photographed. These experiments show that MDC compositions can be used as liver, spleen, and spinal cord soft tissue augmentation materials (FIGS. 8A–8B, 9A–9B, and 10A–10B) to treat various liver, spleen, and spinal cord injuries, diseases, or dysfunctions.

Example 9

MDC Treatment of Bone Defects

Isolation of muscle derived cells: MDC were obtained from mdx mice as described in Example 1.

Clonal isolation of PP6 muscle-derived progenitor cells: To isolate clones from the PP6 cell population, PP6 cells were transfected with a plasmid containing the LacZ, mini-dystrophin, and neomycin resistance genes. Briefly, a SmaI/Sa/I fragment containing the neomycin resistance gene from pPGK-NEO was inserted into the SmaI/Sa/I site in pIEPlacZ plasmid containing the LacZ gene, creating the pNEOlacZ plasmid. The XhoI/Sa/I fragment from DysM3 which contains the short version of the dystrophin gene (K. Yuasa et al., 1998, *FEBS Left*. 425:329–336; gift from Dr. Takeda, Japan) was inserted into Sa/I site in the pNEOlacZ to generate a plasmid which contains the mini-dystrophin, LacZ, and neomycin resistance genes. The plasmid was linearized by Sa/I digestion prior to transfection.

PP6 cells were transfected with 10 µg of the linear plasmid containing mini-dystrophin, LacZ, and neomycin resistance gene using the Lipofectamine Reagent (Gibco BRL) according to the manufacturer's instructions. At 72 hours after transfection, cells were selected with 3000 µg/ml of G418 (Gibco BRL) for 10 days until discrete colonies appeared. Colonies were then isolated and expanded to obtain a large quantity of the transfected cells, and then tested for expression of LacZ. One of these PP6-derived clones, mc13, was used for further study.

Immunohistochemistry: PP6, mc13, and mouse fibroblast cells were plated in a 6-well culture dish and fixed with cold methanol for 1 minute. Cells were then washed with phosphate buffered saline (PBS), and blocked with 5% horse serum at room temperature for 1 hour. The primary antibodies were diluted in PBS as follows: anti-desmin (1:100, Sigma), biotinylated anti-mouse CD34 (1:200, Pharmingen), rabbit anti-mouse Bcl-2 (1:500, Pharmingen), rabbit anti-mouse M-cadherin (1:50, gift from Dr. A. Wernig), mouse anti-mouse MyoD (1:100, Pharmingen), mouse anti-rat myogenin (1:100, Pharmingen), rabbit anti-mouse Flk-1 (1:50, Research Diagnostics), and biotinylated Sca-1 (1:100, Pharmingen). Cells were incubated with the primary antibodies at room temperature overnight. Cells were then washed and incubated with the appropriate biotinylated secondary antibodies for 1 hour at room temperature. Subsequently, the cells were rinsed with PBS then incubated at room temperature with 1/300 streptavidin conjugated with Cy3 fluorochrome for 1 hour. Cells were then analyzed by fluorescence microscopy. For each marker, the percentage of stained cells was calculated for 10 randomly chosen fields of cells.

Cryosections of muscle samples from a four week old normal mouse (C-57 BL/6J, Jackson Laboratories) were fixed with cold acetone for 2 minutes and pre-incubated in 5% horse serum diluted in PBS for 1 hour. For CD34, Bcl-2, and collagen type IV, the following primary antibodies were used: biotin anti-mouse CD34 (1:200 in PBS, Pharmingen), rabbit anti-mouse Bcl-2 (1:1000, Pharmingen), and rabbit anti-mouse collagen type IV (1:100 in PBS, Chemicon). For dystrophin staining, sheep-anti-human DY10 antibody (1:250 dilution in PBS) was used as the primary antibody, and the signal was amplified using anti-sheep-biotin (1:250 dilution in PBS), and streptavidin-FITC (1:250 dilution in PBS).

Stimulation with rhBMP-2, osteocalcin staining, and alkaline phosphatase assay: Cells were plated in triplicate at a density of $1$–$2 \times 10^4$ cells per well in 12 well collagen-coated flasks. The cells were stimulated by the addition of 200 ng/ml recombinant human BMP-2 (rhBMP-2) to the growth medium. The growth medium was changed on days 1, 3, and 5 following the initial plating. A control group of cells was grown in parallel without added rhBMP-2. After 6 days with or without rhBMP-2 stimulation, cells were counted using a microcytometer and analyzed for osteocalcin and alkaline phosphatase expression. For osteocalcin staining, cells were incubated with goat anti-mouse osteocalcin antibodies (1:100 in PBS, Chemicon), followed by incubation with anti-goat antibodies conjugated with the Cy3 fluorochrome. To measure alkaline phosphatase activity, cell lysates were prepared and analyzed using a commercially available kit that utilizes color change in the reagent due to the hydrolysis of inorganic phosphate from p-nitrophenyl phosphate (Sigma). The resulting color change was measured on a spectrophotometer, and the data were expressed as international units ALP activity per liter normalized to $10^6$ cells. Statistical significance was analyzed using student's t-test ($p<0.05$).

In vivo differentiation of mc13 cells in myogenic and osteogenic lineages—Myogenic: The mc13 cells ($5 \times 10^5$ cells) were injected intramuscularly in the hind limb muscle of mdx mice. The animals were sacrificed at 15 days post-injection, and the injected muscle tissue was frozen, cryostat sectioned, and assayed for dystrophin (see above) and LacZ expression. To test for LacZ expression, the muscle sections were fixed with 1% glutaraldehyde and then were incubated with X-gal substrate (0.4 mg/ml 5-bromochloro-3 indolyl-β-D-galactoside (Boehringer-Mannheim), 1 mM $MgCl_2$, 5 mM $K_4Fe(CN)_6$, and 5 mM $K_3Fe(CN)_6$ in phosphate buffered saline) for 1–3 hours. Sections were counter-stained with eosin prior to analysis. In parallel experiments, mc13 cells ($5 \times 10^5$ cells) were injected intravenously in the tail vein of mdx mice. The animals were sacrificed at 7 days post-injection and hind limbs were isolated and assayed for the presence of dystrophin and β-galactosidase as described.

Osteogenic: To construct the adenovirus BMP-2 plasmid (adBMP-2), the rhBMP-2 coding sequence was excised from the BMP-2-125 plasmid (Genetics Institute, Cambridge, Mass.) and subcloned into a replication defective (E1 and E3 gene deleted) adenoviral vector containing the HuCMV promoter. Briefly, the BMP-2-125 plasmid was digested with Sa/I, resulting in a 1237 base pair fragment containing the rhBMP-2 cDNA. The rhBMP-2 cDNA was then inserted into the Sa/I site of the pAd.lox plasmid, which placed the gene under the control of the HuCMV promoter. Recombinant adenovirus was obtained by co-transfection of pAd.lox with psi-5 viral DNA into CREW cells. The resulting adBMP-2 plasmid was stored at −80° C. until further use.

Mc13 cells were trypsinized and counted using a microcytometer prior to infection. Cells were washed several times using HBSS (GibcoBRL). Adenovirus particles equivalent to 50 multiplicity of infection units were premixed into HBSS then layered onto the cells. Cells were incubation at 37° C. for 4 hours, and then incubated with an equal volume of growth medium. Injections of $0.5–1.0 \times 10^6$ cells were performed using a 30-gauge needle on a gas-tight syringe into exposed triceps surae of SCID mice (Jackson Laboratories). At 14–15 days, the animals were anesthetized with methoxyflurane and sacrificed by cervical dislocation. The hind limbs were analyzed by radiography. Subsequently, the triceps surae were isolated and flash frozen in 2-methylbutane buffered in phosphate buffered saline, and pre-cooled in liquid nitrogen. The frozen samples were cut into 5–10 μm sections using a cryostat (Microm, HM 505 E, Fisher Scientific) and stored at −20° C. for further analysis.

RT-PCR analysis: Total RNA was isolated using TRIzol reagent (Life Technologies). Reverse transcription was carried out using SuperScript™ Preamplification System for First Strand cDNA Synthesis (Life Technologies) according to the instructions of the manufacturer. Briefly, 100 ng random hexamers were annealed to 1 μg total RNA at 70° C. for 10 minutes, and then chilled on ice. Reverse transcription was carried out with 2 μl 10×PCR buffer, 2 μl 25 mM MgCl$_2$, 1 μl 10 mM dNTP mix, 2 μl 0.1 M DTT, and 200 U superscript 11 reverse transcriptase. The reaction mixture was incubated for 50 minutes at 42° C.

Polymerase chain reaction (PCR) amplification of the targets was performed in 50 μl reaction mixture containing 2 μl of reverse transcriptase reaction product, 100 μl (5 U) Taq DNA polymerase (Life Technologies), and 1.5 mM MgCl$_2$. The CD34 PCR primers were designed using Oligo software and had the following sequences: CD34 UP: TAA CTT GAC TTC TGC TAC CA (SEQ ID NO:1); and CD34 DOWN: GTG GTC TTA CTG CTG TCC TG (SEQ ID NO:2). The other primers were designed according to previous studies (J. Rohwedel et al., 1995, *Exp. Cell Res.* 220:92–100; D. D. Cornelison et al., 1997, *Dev. Biol.* 191:270–283), and had the following sequences: C-MET UP: GAA TGT CGT CCT ACA CGG CC (SEQ ID NO:3); C-MET DOWN: CAC TAC ACA GTC AGG ACA CTG C (SEQ ID NO:4); MNF UP: TAC TTC ATC AAA GTC CCT CGG TC (SEQ ID NO:5); MNF DOWN: GTA CTC TGG AAC AGA GGC TAA CTT (SEQ ID NO:6); BCL-2 UP: AGC CCT GTG CCA CCA TGT GTC (SEQ ID NO:7); BCL-2 DOWN: GGC AGG TTT GTC GAC CTC ACT (SEQ ID NO:8); MYOGENIN UP: CAA CCA GGA GGA GCG CGA TCT CCG (SEQ ID NO:9); MYOGENIN DOWN: AGG CGC TGT GGG AGT TGC ATT CAC T (SEQ ID NO:10); MYOD UP: GCT CTG ATG GCA TGA TGG ATT ACA GCG (SEQ ID NO:11); and MYOD DOWN: ATG CTG GAC AGG CAG TCG AGG C (SEQ ID NO:12).

The following PCR parameters were used: 1) 94° C. for 45 seconds; 2) 50° C. for 60 seconds (CD34) or 60° C. for 60 seconds (for myogenin and c-met); and 3) 72° C. for 90 seconds for 40 cycles. PCR products were checked by agarose-TBE-ethidium bromide gels. The sizes of the expected PCR products are: 147 bp for CD34; 86 bp for myogenin; and 370 bp for c-met. To exclude the possibility of genomic DNA contamination, two control reactions were completed: 1) parallel reverse transcription in the absence of reverse transcriptase, and 2) amplification of β-actin using an intron-spanning primer set (Clonetech).

Skull defect assay: Three 6–8 week old female SCID mice (Jackson Laboratories) were used in control and experimental groups. The animals were anesthetized with methoxyflurane and placed prone on the operating table. Using a number 10 blade, the scalp was dissected to expose the skull, and the periosteum was stripped. An approximately 5 mm full-thickness circular skull defect was created using a dental burr, with minimal penetration of the dura. A collagen sponge matrix (Helistat™, Colla-T c, Inc.) was seeded with $0.5–1.0 \times 10^6$ MDC either with or without adBMP-2 transduction, and placed into the skull defect. The scalp was closed using a 4-0 nylon suture, and the animals were allowed food and activity. After 14 days, the animals were sacrificed, and the skull specimens were observed and then analyzed microscopically. For von Kossa staining, skull specimens were fixed in 4% formaldehyde and then soaked in 0.1 M AgNo$_3$ solution for 15 minutes. The specimens were exposed to light for at least 15 minutes, washed with PBS, and then stained with hematoxylin and eosin for viewing.

Fluorescence in situ hybridization using Y-probes: The cryosections were fixed for 10 minutes in 3:1 methanol/glacial acetic acid (v:v) and air dried. The sections were then denatured in 70% formamide in 2×SSC (0.3 M NaCl, 0.03 M NaCitrate) pH 7.0 at 70° C. for 2 minutes. Subsequently, the slides were dehydrated with a series of ethanol washes (70%, 80%, and 95%) for 2 minutes at each concentration. The Y-chromosome specific probe (Y. Fan et al., 1996, *Muscle Nerve* 19:853–860) was biotinylated using a BioNick kit (Gibco BRL) according to the manufacturer's instructions. The biotinylated probe was then purified using a G-50 Quick Spin Column (Boehringer-Mannheim), and the purified probe was lyophilized along with 5 ng/ml of sonicated herring sperm DNA. Prior to hybridization, the probe was re-suspended in a solution containing 50% formamide, 1×SSC, and 10% dextran sulfate. After denaturation at 75° C. for 10 minutes, the probe was placed on the denatured sections and allowed to hybridize overnight at 37° C. After hybridization, the sections were rinsed with 2×SSC solution pH 7.0 at 72° C. for 5 minutes. The sections were then rinsed in BMS solution (0.1 M NaHCO$_3$, 0.5 M NaCl, 0.5% NP-40, pH 8.0). The hybridized probe was detected with fluorescein labeled avidin (ONCOR, Inc). The nuclei were counterstained with 10 ng/ml ethidium bromide in Vectashield mounting medium (Vector, Inc).

Marker analysis of mc13 cells: The biochemical markers expressed by mc13, PP6, and fibroblast cells were analyzed using RT-PCR and immunohistochemistry. Table 3 (below) shows that mc13 cells expressed Flk-1, a mouse homologue of the human KDR gene, which was recently identified as a marker of hematopoietic cells with stem cell-like characteristics (B. L. Ziegler et al., supra), but did not express CD34 or CD45. However, other clonal isolates derived from the PP6 MDC of the present invention expressed CD34, as well as other PP6 cell markers. It will be appreciated by those skilled in the art that the procedures described herein can be used to clone out the PP6 muscle-derived progenitor cell population and obtain clonal isolates that express cell markers characteristic of the muscle-derived progenitor cells. Such clonal isolates can be used in accordance with the methods of the invention. For example, the clonal isolates express progenitor cell markers, including desmin, CD34, and Bcl-2. Preferably, the clonal isolates also express the Sca-1 and Flk-1 cell markers, but do not express the CD45 or c-Kit cell markers.

TABLE 3

Cell markers expressed by mdx PP6, mdx mc13, and fibroblast cells.

|  | PP6 cells | | MC13 cells | | Fibroblasts | |
| --- | --- | --- | --- | --- | --- | --- |
|  | imm | RT-PCR | imm | RT-PCR | imm | RT-PCR |
| desmin | + | na | + | na | − | na |
| CD34 | + | + | − | − | − | − |
| Bcl-2 | + | na | +/− | na | − | na |
| Flk-1 | + | na | + | na | − | na |
| Sca-1 | + | na | + | na | − | na |
| M-cadherin | −/+ | na | + | na | − | na |
| Myogenin | +/− | + | +/− | + | − | − |
| c-met | na | + | na | + | na | − |
| MNF | na | + | na | + | na | − |
| MyoD | −/+ | + | na | + | na | − |
| c-Kit | − | na | − | na | na | na |
| CD45 | − | na | − | na | na | na |

Cells were isolated as described above and examined by immunohistochemical analysis. "−" indicates that 0% of the cells showed expression; "+" indicates that >98% of the cells showed expression; "+/−" indicates that 40–80% of the cells showed expression; "−/+" indicates that 5–30% of the cells showed expression; "na" indicates that the data is not available.

Figure 12A:
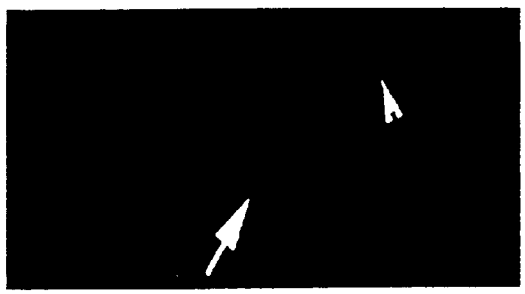
FIGS. 12A–12I illustrate the intracellular co-localization of CD34 or Bcl-2 staining with desmin staining in mouse muscle cells and vascular endothelial cells.
Figure 12B:
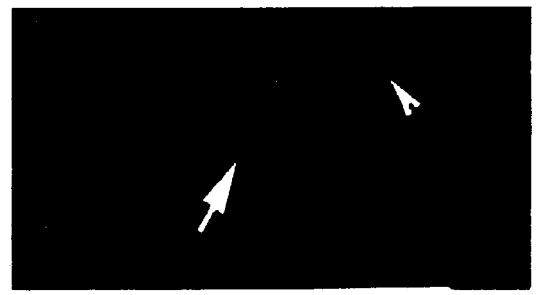
Figure 12C:
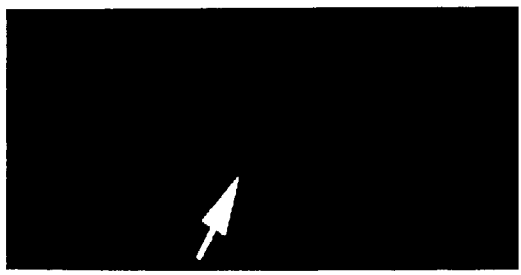
Figure 12D:
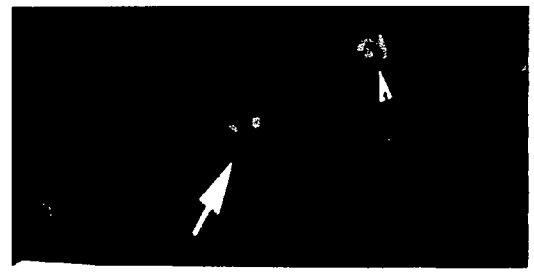
Figure 12E:
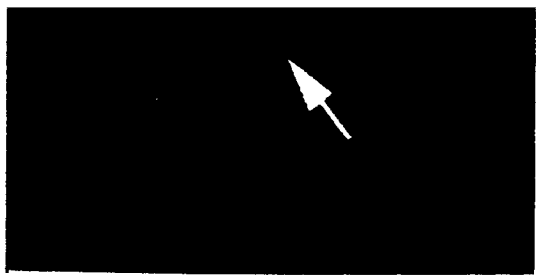
Figure 12F:
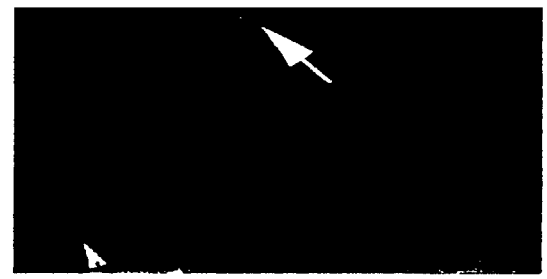
Figure 12G:
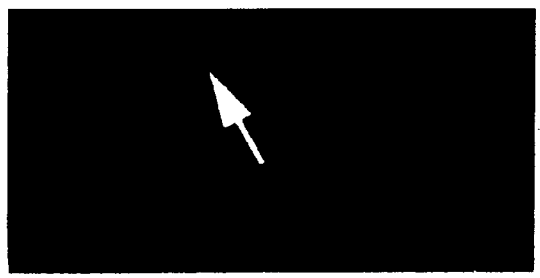
Figure 12H:
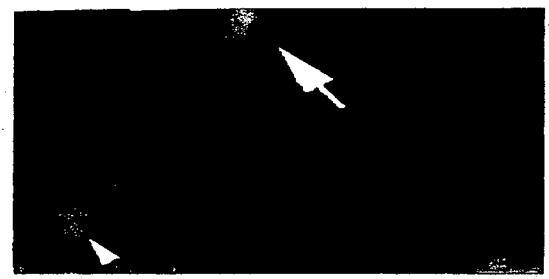
Figure 12I:
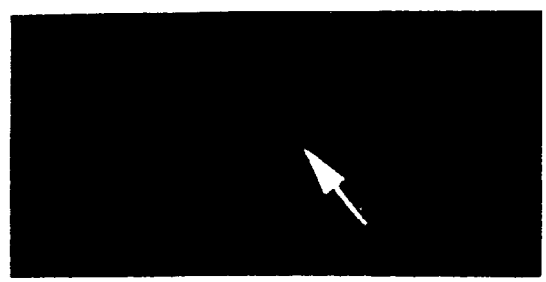

In vivo localization of $CD34^+$ and $Bcl-2^+$ cells: To identify the location of $CD34^+$ and $Bcl-2^+$ cells in vivo, muscle tissue sections from the triceps surae of normal mice were stained using anti-CD34 and anti-Bcl-2 antibodies. The CD34 positive cells constituted a small population of muscle derived cells (FIG. 12A) that were also positive for desmin (FIG. 12B). Co-staining the CD34+, desmin+ cells with anti-collagen type IV antibody localized them within the basal lamina (FIGS. 12B and 12D). As indicated by the arrowheads in FIGS. 12A–D, small blood vessels were also positive for CD34 and collagen type IV, but did not co-localize with the nuclear staining. The expression of CD34 by vascular endothelial cells has been shown in previous studies (L. Fina et al., supra). The Bcl-2+, desmin+ cells were similarly identified (FIGS. 12E–12H) and localized within the basal lamina (FIGS. 12F and 12H). The sections were also stained for M-cadherin to identify the location of satellite cells (FIG. 12I). The satellite cells were identified at similar locations as CD34+, desmin+, or Bcl-2+, desmin+ cells (arrow, FIG. 12I). However, multiple attempts to co-localize CD34 or Bcl-2 with M-cadherin were unsuccessful, suggesting that M-cadherin expressing cells do not co-express either Bcl-2 or CD34. This is consistent with PP6 cells expressing high levels of CD34 and Bcl-2, but expressing minimal levels of M-cadherin, as disclosed herein.

Figure 13A:
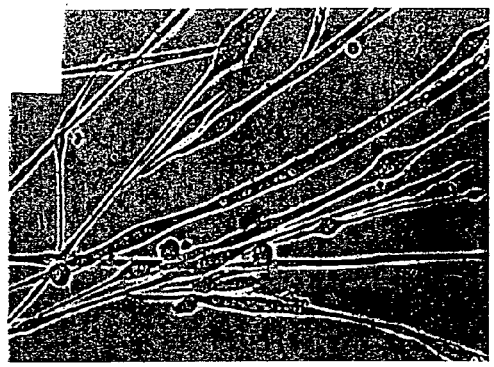
FIGS. 13A–E illustrate the morphologic changes and expression of osteocalcin resulting from the exposure of mc13 cells to rhBMP-2. Mc13 cells were incubated in growth media with or without rhBMP-2 for 6 days.
Figure 13B:
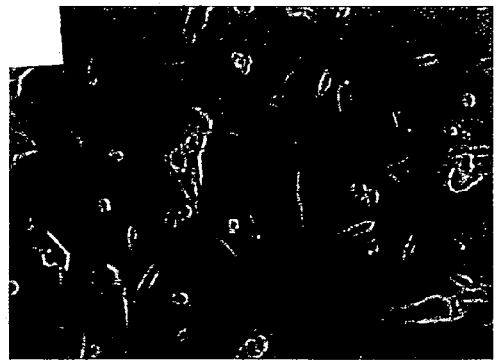
Figure 13C:
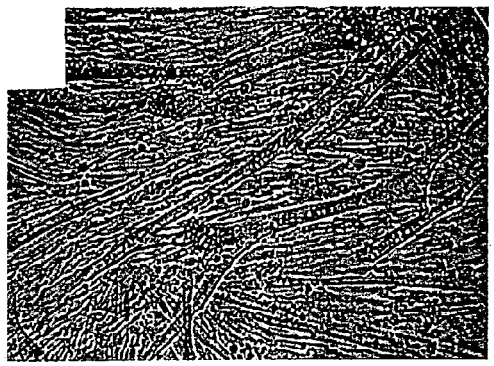
Figure 13D:
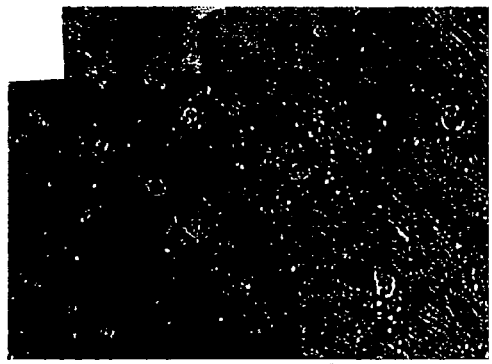
Figure 13E:
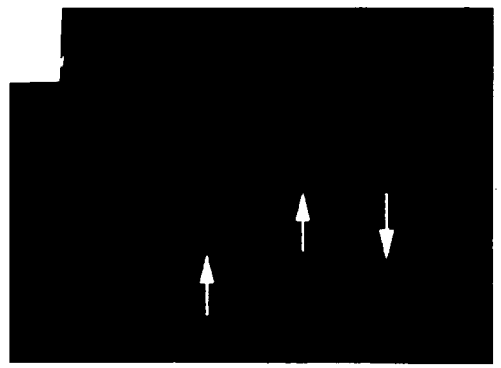

In vitro differentiation of clonal muscle progenitor cells into osteogenic lineage: Mc13 cells were assessed for osteogenic differentiation potential by stimulation with rhBMP-2. Cells were plated on 6-well culture dishes and grown to confluency in the presence or absence of 200 ng/ml rhBMP-2. Within 34 days, mc13 cells exposed to rhBMP-2 showed dramatic morphogenic changes compared to cells without rhBMP-2. In the absence of rhBMP-2, mc13 cells began to fuse into multinucleated myotubes (FIG. 13A). When exposed to 200 ng/ml rhBMP-2, however, cells remained mononucleated and did not fuse (FIG. 13B). When cell density reached >90% confluency, the untreated culture fused to form multiple myotubes (FIG. 13C), while the treated cells became circular and hypertrophic (FIG. 13D). Using immunohistochemistry, these hypertrophic cells were analyzed for the expression of osteocalcin. Osteocalcin is a matrix protein that is deposited on bone, specifically expressed by osteoblasts. In contrast to the untreated group, the rhBMP-2 treated hypertrophic cells showed significant expression of osteocalcin (FIG. 13E), thus suggesting that mc13 cells are capable of differentiating into osteoblasts upon exposure to rhBMP-2.

Mc13 cells were then analyzed for expression of desmin following rhBMP-2 stimulation. Newly isolated mc13 cells showed uniform desmin staining (FIGS. 14A and 14B). Within 6 days of exposure to rhBMP-2, only 30–40% of mc13 cells showed desmin staining. In the absence of rhBMP-2 stimulation, approximately 90–100% of mc13 cells showed desmin staining (FIG. 14C). This result suggests that stimulation of mc13 cells with rhBMP-2 results in the loss of myogenic potential for these cells.

In addition, mc13 cells were analyzed for the expression of alkaline phosphatase following rhBMP-2 stimulation. Alkaline phosphatase has been used as a biochemical marker for osteoblastic differentiation (T. Katagiri et al., 1994, *J. Cell Biol.* 127:1755–1766). As shown in FIG. 14D, alkaline phosphatase expression of mc13 cells was increased more than 600 fold in response to rhBMP-2. PP1–4 cells, used as a control, did not show increased alkaline phosphatase activity in response to rhBMP-2 (FIG. 14D). Taken together, these data demonstrate that cells of a PP6 clonal isolate, e.g., mc13 cells, can lose their myogenic markers and differentiate through the osteogenic lineage in response to rhBMP-2 exposure in vitro.

In vivo differentiation of mc13 cells into myogenic and osteogenic lineages: To determine whether mc13 cells were capable of differentiating through the myogenic lineage in vivo, the cells were injected into the hind limb muscle tissue of mdx mice. The animals were sacrificed 15 days following injection, and their hind limbs were harvested for histological and immunohistochemical analysis. Several myofibers showed LacZ and dystrophin staining in the region surrounding the injection site (FIGS. 15A and 15B), indicating that mc13 cells can differentiate through the myogenic lineage in vivo and enhance muscle regeneration and restore dystrophin in the dystrophic muscle.

In a parallel experiment, mc13 cells were injected intravenously into the tail vein of mdx mice. The animals were sacrificed at 7 days post-injection, and the hind limb muscles were harvested for histological and immunohistochemical analysis. Several hind limb muscle cells showed LacZ and dystrophin staining (FIGS. 15C–15D; see also "*"), suggesting that mc13 cells can be delivered systemically to the target tissue for rescue of dystrophin expression.

To test the pluripotent characteristics of mc13 cells in vivo, the cells were transduced with an adenoviral vector encoding rhBMP-2 (adBMP-2). The mc13 cells with adBMP-2 were then injected into hind limbs of SCID mice. The animals were sacrificed at 14 days post-injection, and the hind limbs were removed for histochemical and immunochemical analysis. Enzyme-linked immunosorbent assay (ELISA) analysis of mc13 cells transduced with adBMP-2 showed that infected cells were capable of producing rhBMP-2. Radiographic analysis of hind limbs of injected SCID mice revealed robust ectopic bone formation within 14 days of injection (FIG. 15E). Histological analysis using LacZ staining of the ectopic bone shows that LacZ positive mc13 cells were uniformly located within the mineralized matrix or lacunae, a typical location where osteoblasts and osteocytes are found (FIG. 15F).

To further confirm the role of mc13 in formation of the ectopic bone, the muscle sections were also stained for presence of dystrophin. As shown in FIG. 15G, the ectopic bone contained cells highly positive for dystrophin, suggesting that mc13 cells are intimately participating in bone formation. As a control, similar experiments were carried out with fibroblasts. Fibroblasts were found to support robust ectopic bone formation, but the injected cells were uniformly found outside of the bone, and none could be located within the mineralized matrix. This suggests that the fibroblasts are capable of delivering rhBMP-2 to form ectopic bone, but are unable to differentiate into osteoblasts. In this case, the cells participating in mineralization of the ectopic bone are most likely derived from the host tissue. Thus, these results demonstrate that mc13 cells can differentiate into osteoblasts, both in vivo and in vitro, Enhancement of bone healing by genetically engineered muscle-derived cells: Skull defects (approximately 5 mm) were created in skeletally mature (6–8 weeks old) female SCID mice using a dental burr as described above. Previous experiments have demonstrated that 5 mm skull defects are "non-healing" (P. H. Krebsbach et al., 1998, Transplantation 66:1272–1278). The skull defect was filled with a collagen sponge matrix seeded with mc13 cells transduced or not transduced with adBMP-2. These mice were sacrificed at 14 days, and the healing of the skull defect was analyzed. As shown in FIG. 16A, the control group treated with mc13 cells without rhBMP-2 showed no evidence of healing of the defect. In contrast, the experimental group treated with mc13 cells transduced to express rhBMP-2 showed almost a full closure of the skull defect at 2 weeks (FIG. 16B). The von Kossa staining, which highlights mineralized bone, showed robust bone formation in the group treated with mc13 cells transduced to express rhBMP-2 (FIG. 16D), but minimal bone formation was observed in the control group (FIG. 16C).

The area of new bone in the experimental group was analyzed by fluorescence in situ hybridization (FISH) with a Y-chromosome specific probe to identify transplanted cells. As shown in FIG. 16E, Y-chromosome positive cells were identified within the newly formed bone, indicating active participation of transplanted cells in bone formation under the influence of rhBMP-2. The Y-chromosome negative cells were also identified within the newly formed skull, thus indicating active participation of host-derived cells as well. These results demonstrate that mc13 cells can mediate healing of a "non-healing" bone defect upon stimulation with rhBMP-2, and indicate that the MDC of the present invention can be used in the treatment of bone defects, injuries, or traumas.

All patent applications, patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

What is claimed is:

1. A method of isolating an end population of skeletal muscle-derived progenitor cells (MDCs), comprising:
    (a) plating a suspension of skeletal muscle cells from skeletal muscle tissue in a first container to which fibroblast cells of the skeletal muscle cell suspension adhere,
    (b) re-plating non-adherent cells from step (a) in a second container, wherein the step of re-plating is after 15–20% of cells have adhered to the first container;
    (c) repeating step (b) at least once;
    (d) isolating the skeletal muscle-derived MDCs.

2. A method of isolating an end population of muscle-derived progenitor cells (MDCs), comprising:
    (a) plating a suspension of muscle cells from skeletal muscle tissue in a first collagen-coated container to which fibroblast cells of the muscle cell suspension adhere;
    (b) re-plating non-adherent cells from step (a) in a second collagen-coated container, wherein the step of re-plating is after 30–40% of cells have adhered to the first container;
    (c) repeating step (b) at least once to enrich for an end population of viable, non-fibroblast, desmin-expressing cells in the second container; and
    (d) isolating the MDCs as the end population of viable, non-fibroblast, desmin-expressing cells.

3. The method according to claim 1, wherein step (b) is repeated at least five times.

4. The method according to claim 1, wherein the MDCs are introduced into an area of muscle tissue selected from the group consisting of esophageal muscle tissue, gastroesophageal muscle tissue, sphincter muscle tissue, bladder muscle tissue, ureteral-bladder tissue and skin tissue to augment or bulk the tissue.

5. The method according to claim 1, further comprising the step of isolating a clonal population of MDCs.

6. The method according to claim 5, wherein the clonal population of MDCs is introduced into an area of muscle tissue selected from the group consisting of esophageal muscle tissue, gastroesophageal muscle tissue, sphincter muscle tissue, bladder muscle tissue, ureteral-bladder tissue and skin tissue to augment or bulk the tissue.

7. The method according to claim 2, wherein step (b) is repeated at least five times.

8. The method according to claim 2, wherein the MDCs are introduced into an area of muscle tissue selected from the group consisting of esophageal muscle tissue, gastroesophageal muscle tissue, sphincter muscle tissue, bladder muscle tissue, ureteral-bladder tissue and skin tissue to augment or bulk the tissue.

9. The method according to claim 2, further comprising the step of isolating a clonal population of MDCs.

10. The method according to claim 9, wherein the clonal population of MDCs is introduced into an area of muscle tissue selected from the group consisting of esophageal muscle tissue, gastroesophageal muscle tissue, sphincter muscle tissue, bladder muscle tissue, ureteral-bladder tissue and skin tissue to augment or bulk the tissue.

* * * * *

UNITED STATES PATENT AND TRADEMARK OFFICE
CERTIFICATE OF CORRECTION

| | | |
|---|---|---|
| PATENT NO. | : 7,115,417 B1 | |
| APPLICATION NO. | : 09/549937 | |
| DATED | : October 3, 2006 | |
| INVENTOR(S) | : Michael B. Chancellor et al. | |

It is certified that error appears in the above-identified patent and that said Letters Patent is hereby corrected as shown below:

On Title Page, Item (54), the title

SOFT TISSUE AND BONE AUGMENTATION AND BULKING UTILIZING MUSCLE-DERIVED PROGENITO COMPOSITIONS, AND TREATMENTS THEREOF

Should read

-- SOFT TISSUE AND BONE AUGMENTATION AND BULKING UTILIZING MUSCLE-DERIVED PROGENITOR CELLS, COMPOSITIONS, AND TREATMENTS THEREOF --.

Col. 1, lines 12-14, before field of Invention, insert

--GOVERNMENT INTERESTS
    This invention was made with Government support under Grant No. DK055387 awarded by the National Institute of Health. The Government has certain rights in this invention.--

Signed and Sealed this

Sixth Day of February, 2007

JON W. DUDAS
*Director of the United States Patent and Trademark Office*